US007863418B2

(12) United States Patent
Utku et al.

(10) Patent No.: US 7,863,418 B2
(45) Date of Patent: Jan. 4, 2011

(54) T-CELL MEMBRANE PROTEIN (TIRC7) AND PEPTIDES DERIVED THEREFROM

(75) Inventors: Nalan Utku, Pfalzburger Strasse 81, Berlin (DE) D-10719; Steven R. Gullans, Natick, MA (US); Edgar L. Milford, Dover, MA (US)

(73) Assignees: The Brigham and Women's Hospital, Inc., Boston, MA (US); Nalan Utku, Berlin (DE)

( * ) Notice: Subject to any disclaimer, the term of this patent is extended or adjusted under 35 U.S.C. 154(b) by 424 days.

(21) Appl. No.: 11/126,866

(22) Filed: May 10, 2005

(65) Prior Publication Data
US 2005/0220789 A1 Oct. 6, 2005

Related U.S. Application Data

(60) Continuation of application No. 10/145,012, filed on May 13, 2002, now abandoned, which is a division of application No. 09/510,646, filed on Feb. 23, 2000, now abandoned, which is a continuation of application No. PCT/EP98/05462, filed on Aug. 19, 1998.

(51) Int. Cl.
*C07K 14/705* (2006.01)
*A61K 38/17* (2006.01)
(52) U.S. Cl. .................................... 530/350; 514/12
(58) Field of Classification Search .................. None
See application file for complete search history.

(56) References Cited

U.S. PATENT DOCUMENTS

| 5,183,657 | A | 2/1993 | Burrman |
| 5,747,034 | A | 5/1998 | de Boer et al. |
| 5,827,516 | A | 10/1998 | Urban et al. |
| 6,777,537 | B1 * | 8/2004 | Stashenko et al. ............ 530/350 |
| 2003/0124614 | A1 | 7/2003 | Utku et al. |
| 2005/0048067 | A1 | 3/2005 | Utku et al. |
| 2006/0292143 | A1 * | 12/2006 | Utku et al. ............... 424/144.1 |

FOREIGN PATENT DOCUMENTS

| WO | WO 9423033 | 10/1994 |
| WO | WO 9803651 | 1/1998 |

OTHER PUBLICATIONS

Attwood T., Science 2000; 290:471-473.*
Skolnick et al., Trends in Biotech. 2000; 18(1):34-39.*
Blazer et al., J. Immunol., 1996, 157: 3250-3259.*
Sequence aligment, 2 pages, (2008).*
Jeffrey A. Blueston and Jeffrey B. Matthews (2000), "Editorial" *Clinical Immunology*, vol. 96(3): 171-173.
Cohen, IR and Miller, A. "Autoimmune Disease Models", *Academic Press Limited*, 1994 (preface).
Cramer, DV, Podesta, LG, and Makowka, L. "Handbook of Animal Models In Transplantation Research" *CRC Press Inc.* 1994 (p. 8).

Mohamed H. Sayegh, et al. (1995) "CD28-B7 Blockade After Alloantigenic Challenge In Vivo Inhibits Th1 Cytokines but Spares Th2" *J. Exp. Med* 181: 1869-1874.
Kirk et al. (1997) "CTLA4-Ig and anti-CD40 Ligand Prevent Renal Allograft Rejection in Primates", *Proc. Natl. Acad. Sci. USA* 94:8789-8794.
Filmore, D (2004) "It's a GPOCR World" *Modern Drug Discovery* 7(11): 24-28.
Pending Claims in U.S. Appl. No. 11/510,868, published as U.S. Patent Publication No. 2006/0292143 for Utku et al., (2006).
Dec. 12, 1998 International Search Report in connection with International Application No. PCT/EP98/05462.
Dec. 29, 1999 International Preliminary Examination Report in connection with International Application No. PCT/EP98/05462.
Aug. 11, 1999 Written Opinion in connection with International Application No. PCT/EP98/05462.
Nov. 10, 1999 Response to Aug. 11, 1999 Written Opinion in connection with International Application No. PCT/EP98/05462.
Nov. 25, 1999 Written Opinion in connection with International Application No. PCT/EP98/05462.
Dec. 10, 1999 Response to Nov. 25, 1999 Written Opinion in connection with International Application No. PCT/EP98/05462.
Mar. 5, 2002 European Patent Office Communication pursuant to Article 96(2) EPC in connection with European Application No. EP 98 945 293.
Jun. 27, 2002 Response to the Mar. 5, 2002 Communication pursuant to Article 96(2) EPC in connection with European Application No. EP 98 945 293.
Database Embl [Online] ID No. HS1196311, AC No. AA293678, Apr. 22, 1997 Hillier L et al:'*Homo sapiens* cDNA clone similar to specific 116-kDa vacuolar proton pump subunit'.
Database Embl [Online] AC No. A1088498, Aug. 19, 1998 NCI-CGAP:'*Homo Sapiens* cDNA clone similar to specific 116-kDa vacuolar proton pump subunit'.
Heinemann, T. et al., "Genomic organization of the gene coding for TIRC7, a novel membrane protein essential for T cell activation", May 1999, Genomics 57:398-406, XP000999606.
Nov. 6, 2000 Examiner's Report in connection with Australian Patent Application No. 92654/98.
Sep. 12, 2001 Response to Examiner's Nov. 6, 2000 Report filed in connection with Australian Patent Application No. 92654/98.
Sep. 21, 2001 Examiner's Report in connection with Australian Patent Application No. 92654/98.
Oct. 29, 2001 Response to Examiner's Sep. 21, 2001 Report filed in connection with Australian Patent Application No. 92654/98.

(Continued)

*Primary Examiner*—Ilia Ouspenski
(74) *Attorney, Agent, or Firm*—John P. White; Cooper & Dunham LLP

(57) ABSTRACT

Described are a T cell immune response cDNA 7 (TIRC7) encoding a T-cell transmembrane protein, peptides and polypeptides derived therefrom and antibodies recognizing such (poly)peptides. Peptides, polypeptides and antibodies capable of inhibiting T-cell stimulation through the T-cell membrane protein (TIRC7) are provided. Vectors comprising polynucelotides encoding such polypeptides and peptides, host cells transformed therewith, and their use in the production of such, peptides or polypeptides are also described.

6 Claims, 14 Drawing Sheets

OTHER PUBLICATIONS

Nov. 9, 2001 Examiner's Report in connection with Australian Patent Application No. 92654/98.
Jun. 5, 2002 Response to Examiner's Nov. 9, 2001 Report in connection with Australian Patent Application No. 92654/98.
Amac, N. et al., "Identification of a New Human (H+)—ATPase Proton Pump Homology Differentially Expressed in Alloactivated Lymphocytes", Abstract for the American Society of Nephrology 27th Annual Meeting, Oct. 26-29, 1994, J. Am. Soc. Nephrology, Sep. 5 (3):740.
N. Utku Amac et al., "Characterization of a Novel Human Gene (C7) Associated with Early Lymphocyte Activation", Abstract for the Fifteenth Annual Meeting of the American Society of Transplant Physicians, May 27-30, 1996, No. P-6, p. 174.
Utku, Nalan et al., "Identification of T Cell Immune Response cDNA (TIRC7) in Alloactivated Human Lymphocytes", Fifth Basic Sciences Symposium of the Transplantation Society, Program & Poster Abstracts, Sep. 6-11, 1997.
Utku, N. et al., "Characterization of a Novel T Cell Immune Response cDNA (TIRC7) Associated with Early Lymphocyte Activation", Fourth International Symposium on Clinical Immunology, Jun. 19-22, '97.
N. Utku, et al., "Identification of T-cell immune response cDNA (TIRC-7) in allocativated human lymphocytes", Abstract, Congress of Molecular Medicine, Berlin May 3-5, 1997.
Utku, N. et al., "Characterization of a Novel T-Cell Immune Response cDNA (TIRC7) Associated with Early Lymphocyte Activation", XIIIth Spring Meeting of the Deutsche Gasellschaft für Immunologie, Mar. 6-8, 1997, (Abstract).
Utku, N. et al., "Antibodies to a Novel T Cell Antigen, TIRC7, Block Selectively TYP 1 But Not TYP 2 T-Cell Activation and Prolongs Allograft Survival", Abstract for the 17th Annual Scientific Meeting, (1998).
Anan Chuntharapai and K. Jin Kim, "Generation of Monoclonal Antibodies to Chemokine Receptors", Methods in Enzymology, vol. 288, (1997), pp. 15-27.
Kumamoto, Yusuke et al., "Monoclonal Antibody Specific for TIRC7 Induces Donor-specific Anergy and Prevents Rejection of Cardiac Allografts in Mice", American Journal of Transplantation, (2004), vol. 4, pp. 505-514.
Utku, Nalan et al., "TIRC7 Deficiency Causes In Vitro and In Vivo Augmentation of T and B Cell Activation and Cytokine Response", The Journal of Immunology, vol. 173, (2004), pp. 2342-2352.
Utku, Nalan et al., "Prevention of Acute Allograft Rejection by Antibody Targeting of TIRC7", a Novel T Cell Membrane Protein, Immunity, vol. 9, (1998), pp. 509-518.
Yi-Ping Li et al., "Molecular cloning and characterization of a putative novel human osteoclast-specific 116-kDa vacuolar proton pump subunit", Biochemical and Biophysical Research Communications, vol. 218, No. 3, (1996), pp. 813-821.
Chong-Kil Lee et al., "Cloning of a cDNA for a T cell produced molecule with a putative immune regulatory role", *Molecular Immunology*, vol. 27, No. 11, (1990), pp. 1137-1144.
U.S. Appl. No. 11/126,841, Nalan Utku et al.
Sato S.B. and Toyama s. (1994) Inter.WithTheEndo.Acidif. ByAMonoclon.Antib.Direc.Towrd.The 116 (100) -kD Subunt. OfTheVacuo.TypePrtn.Pump,TheJ.OfCellBio.,V.127(1), pp. 39-53.
Claims pending in U.S. Appl. No. 10/489,725, (as of 2009).

* cited by examiner

```
                              GGACGCCCCTGCTCCAGGCCCCCGGGGGCCGCACCAGGACCTGAG  46
GGTCAAGTGAGTGAGGGATGACCTCATGCCCTTTCTGGCCAGCCCAGAACCCCTGGCCAGTCGCTGGGCT  116
GGGCCAGGCTGAGCTCCGACTCCTTGTCCAGTGCTCTCCCCAGGCTGGCCCCGCCTCCTCCTTCAGGCCC  186
GGAACTTCCCACAGTCCCAAGCCCTAGCCCTAGGGGGTTCTCCTCTTCTGGTCCTGCCCGGGAGGCCTCC  256
TGCCTTCCCCTGTGGGCAGGGCCAGTGTGCCCAATTGCCCGATTGCCCGTGCTGGGCAGGGTCCTGCCCG  326
GGGGGCCTGGTGGGGGAGGCAGGGCAGGAGGTTGGAGCAGCCCTGCCCAGCCCCGTGGCCGCCAGCTTTG  396
TGGCAGGTGCCGTGGAGCCCCACAAGGCCCCTGCCCTAGAGCGCCTGCTCTGGAGGGCCTGCCGCGGCTT  466
CCTCATTGCCAGCTTCAGGGAGCTGGAGCAGCCGCTGGAGCACCCCGTGACGGGCGAGCCAGCCACGTGG  536
ATGACCTTCCTCATCTCCTACTGGGGTGAGCAGATCGGACAGAAGATCCGCAAGATCACGGACTGCTTCC  606
  M   T   F   L   I   S   Y   W   G   E   Q   I   G   Q   K   I   R   K   I   T   D   C   F   H
ACTGCCACGTCTTCCCGTTTCTGCAGCAGGAGGAGGCCCGCCTCGGGGCCCTGCAGCAGCTGCAACAGCA  676
    C   H   V   F   P   F   L   Q   Q   E   E   A   R   L   G   A   L   Q   Q   L   Q   Q   Q
GAGCCAGGAGCTGCAGGAGGTCCTCGGGGAGACAGAGCGGTTCCTGAGCCAGGTGCTAGGCCGGGTGCTG  746
    S   Q   E   L   Q   E   V   L   G   E   T   E   R   F   L   S   Q   V   L   G   R   V   L
CAGCTGCTGCCGCCAGGGCAGGTGCAGGTCCACAAGATGAAGGCCGTGTACCTGGCCCTGAACCAGTGCA  816
    Q   L   L   P   P   G   Q   V   Q   V   H   K   M   K   A   V   Y   L   A   L   N   Q   C   S
GCGTGAGCACCACGCACAAGTGCCTCATTGCCGAGGCCTGGTGCTCTGTGCGAGACCTGCCCGCCCTGCA  886
    V   S   T   T   H   K   C   L   I   A   E   A   W   C   S   V   R   D   L   P   A   L   Q
GGAGGCCCTGCGGGACAGCTCGATGGAGGAGGGAGTGAGTGCCGTGGCTCACCGCATCCCTGCCGGGAC  956
    E   A   L   R   D   S   S   M   E   E   G   V   S   A   V   A   H   R   I   P   C   R   D
ATGCCCCCCACACTCATCCGCACCAACCGCTTCACGGCCAGCTTCCAGGGCATCGTGGATGCCTACGGCG  1026
    M   P   P   T   L   I   R   T   N   R   F   T   A   S   F   Q   G   I   V   D   A   Y   G   V
TGGGCCGCTACCAGGAGGTCAACCCCGCTCCCTACACCATCATCACCTTCCCCTTCCTGTTTGCTGTGAT  1096
      G   R   Y   Q   E   V   N   P   A   P   Y   T   I   I   T   F   P   F   L   F   A   V   M
GTTCGGGGATGTGGGCCACGGGCTGCTCATGTTCCTCTTCGCCCTGGCCATGGTCCTTGCGGAGAACCCA  1166
    F   G   D   V   G   H   G   L   L   M   F   L   F   A   L   A   M   V   L   A   E   N   R
CCGGCTGTGAAGGCCGCGCAGAACGAGATCTGGCAGACTTTCTTCAGGGGCCGCTACCTGCTCCTGCTTA  1236
    P   A   V   K   A   A   Q   N   E   I   W   Q   T   F   F   R   G   R   Y   L   L   L   M
TGGGCCTGTTCTCCATCTACACCGGCTTCATCTACAACGAGTGCTTCAGTCGCGCCACCAGCATCTTCCC  1306
      G   L   F   S   I   Y   T   G   F   I   Y   N   E   C   F   S   R   A   T   S   I   F   P
CTCGGGCTGGAGTGTGGCCGCCATGGCCAACCAGTCTGGCTGGAGTGATGCATTCCTGGCCCAGCACACG  1376
    S   G   W   S   V   A   A   M   A   N   Q   S   G   W   S   D   A   F   L   A   Q   H   T
ATGCTTACCCTGGATCCCAACGTCACCGGTGTCTTCCTGGGACCCTACCCCTTTGGCATCGATCCTATTT  1446
    M   L   T   L   D   P   N   V   T   G   V   F   L   G   P   Y   P   F   G   I   D   P   I   W
GGAGCCTGGCTGCCAACCACTTGAGCTTCCTCAACTCCTTCAAGATGAAGATGTCCGTCATCCTGGGCGT  1516
      S   L   A   A   N   H   L   S   F   L   N   S   F   K   M   K   M   S   V   I   L   G   V
CGTGCACATGGCCTTTGGGGTGGTCCTCGGAGTCTTCAACCACGTGCACTTTGGCCAGAGGCACCGGCTG  1586
    V   H   M   A   F   G   V   V   L   G   V   F   N   H   V   H   F   G   Q   R   H   R   L
CTGCTGGAGACGCTGCCGGAGCTCACCTTCCTGCTGGGACTCTTCGGTTACCTCGTGTTCCTAGTCATCT  1656
    L   L   E   T   L   P   E   L   T   F   L   L   G   L   F   G   Y   L   V   F   L   V   I   Y
ACAAGTGGCTGTGTGTCTGGGCTGCCAGGGCCGCCTCGGCCCCCAGCATCCTCATCCACTTCATCAACAT  1726
      K   W   L   C   V   W   A   A   R   A   A   S   A   P   S   I   L   I   H   F   I   N   M
GTTCCTCTTCTCCCACAGCCCCAGCAACAGGCTGCTCTACCCCCGGCAGGAGGTGGTCCAGGCCACGCTG  1796
    F   L   F   S   H   S   P   S   N   R   L   L   Y   P   R   Q   E   V   V   Q   A   T   L
GTGGTCCTGGCCTTGGCCATGGTGCCCATCCTGCTGCTTGGCACACCCCTGCACCTGCTGCACCGCCACC  1866
    V   V   L   A   L   A   M   V   P   I   L   L   L   G   T   P   L   H   L   L   H   R   H   R
GCCGCCGCCTGCGGAGGAGGCCCGCTGACCGACAGGAGGAAAACAAGGCCGGGTTGCTGGACCTGCCTGA  1936
      R   R   L   R   R   R   P   A   D   R   Q   E   E   N   K   A   G   L   L   D   L   P   D
CGCATCTGTGAATGGCTGGAGCTCCGATGAGGAAAAGGCAGGGGGCCTGGATGATGAAGAGGAGGCCGAG  2006
    A   S   V   N   G   W   S   S   D   E   E   K   A   G   L   D   D   E   E   A   E
CTCGTCCCCTCCGAGGTGCTCATGCACCAGGCCATCCACACCATCGAGTTCTGCCTGGGCTGCGTCTCCA  2076
    L   V   P   S   E   V   L   M   H   Q   A   I   H   T   I   E   F   C   L   G   C   V   S   N
ACACCGCCTCCTACCTGCGCCTGTGGGCCCTGAGCCTGGCCCACGCCCAGCTGTCCGAGGTTCTGTGGGC  2146
      T   A   S   Y   L   R   L   W   A   L   S   L   A   H   Q   L   S   E   V   L   W   A
CATGGTGATGCGCATAGGCCTGGGCCTGGGCCGGAGGTGGGCGTGGCGGCTGTGGTGCTGGTCCCCATC  2216
    M   V   M   R   I   G   L   G   L   G   R   E   V   G   V   A   A   V   V   L   V   P   I
TTTGCCGCCTTTGCCGTGATGACCGTGGCTATCCTGCTGGTGATGGAGGGACTCTCAGCCTTCCTGCACG  2286
    F   A   A   F   A   V   M   T   V   A   I   L   L   V   M   E   G   L   S   A   F   L   H   A
CCCTGCGGCTGCACTGGGTGGAATTCCAGAACAAGTTCTACTCAGGCACGGGCTACAAGCTGAGTCCCTT  2356
      L   R   L   H   W   V   E   F   Q   N   K   F   Y   S   G   T   G   Y   K   L   S   P   F
CACCTTCGCTGCCACAGATGACTAGGGCCCACTGCAGGTCCTGCCAGACCTCCTTCCTGACCTCTGAGGC  2426
    T   F   A   A   T   D   D
AGGAGAGGAATAAAGACGGTCCGCCCTGGCAAAAAAAAAAAAAAAAAAAAAAAAAAAAAAAAAAAAA     2488
```

Figure 1 B

Histological analysis of kidney allograft
- control antibody treated rats -

Histological analysis of kidney allograft
- anti-TIRC7 antibody treated rats -

SEQUENCE LISTING

```
<160> NUMBER OF SEQ ID NOS: 13

<210> SEQ ID NO 1
<211> LENGTH: 2488
<212> TYPE: DNA
<213> ORGANISM: Homo sapiens
<220> FEATURE:
<221> NAME/KEY: CDS
<222> LOCATION: (537)..(2378)

<400> SEQUENCE: 1 ggacgccct  gctccaggcc  cccggggggc  cgcaccagga  cctgagggtc  aagtgagtga      60
gggatgacct  catgcccttt  ctggccagcc  cagaacccct  ggccagtcgc  tgggctgggc     120
caggctgagc  tccgactcct  tgtccagtgc  tctcccagg   ctggccccgc  ctcctccttc     180
aggcccggaa  cttcccacag  tcccaagccc  tagccctagg  gggttctcct  cttctggtcc     240
tgcccgggag  gcctcctgcc  ttccctgtg   ggcagggcca  gtgtgcccaa  ttgcccgatt     300
gcccgtgctg  ggcagggtcc  tgcccggggg  gcctggtggg  ggaggcaggg  caggaggttg     360
gagcagccct  gcccagcccc  gtggccgcca  gctttgtggc  aggtgccgtg  gagcccaca      420 aggcccctgc  cctagagcgc  ctgctctgga  gggcctgccg  cggcttcctc  attgccagct     480
tcagggagct  ggagcagccg  ctggagcacc  ccgtgacggg  cgagccagcc  acgtgg atg     539
```

-continued

```
                                                                                    Met
                                                                                      1
acc ttc ctc atc tcc tac tgg ggt gag cag atc gga cag aag atc cgc        587
Thr Phe Leu Ile Ser Tyr Trp Gly Glu Gln Ile Gly Gln Lys Ile Arg
          5                   10                  15 aag atc acg gac tgc ttc cac tgc cac gtc ttc ccg ttt ctg cag cag        635
Lys Ile Thr Asp Cys Phe His Cys His Val Phe Pro Phe Leu Gln Gln
         20                  25                  30 gag gag gcc cgc ctc ggg gcc ctg cag cag ctg caa cag cag agc cag        683
Glu Glu Ala Arg Leu Gly Ala Leu Gln Gln Leu Gln Gln Gln Ser Gln
     35                  40                  45 gag ctg cag gag gtc ctc ggg gag aca gag cgg ttc ctg agc cag gtg        731
Glu Leu Gln Glu Val Leu Gly Glu Thr Glu Arg Phe Leu Ser Gln Val
 50                  55                  60                  65 cta ggc cgg gtg ctg cag ctg ctg ccg cca ggg cag gtg cag gtc cac        779
Leu Gly Arg Val Leu Gln Leu Leu Pro Pro Gly Gln Val Gln Val His
                 70                  75                  80 aag atg aag gcc gtg tac ctg gcc ctg aac cag tgc agc gtg agc acc        827
Lys Met Lys Ala Val Tyr Leu Ala Leu Asn Gln Cys Ser Val Ser Thr
             85                  90                  95 acg cac aag tgc ctc att gcc gag gcc tgg tgc tct gtg cga gac ctg        875
Thr His Lys Cys Leu Ile Ala Glu Ala Trp Cys Ser Val Arg Asp Leu
        100                 105                 110 ccc gcc ctg cag gag gcc ctg cgg gac agc tcg atg gag gag gga gtg        923
Pro Ala Leu Gln Glu Ala Leu Arg Asp Ser Ser Met Glu Glu Gly Val
115                 120                 125 agt gcc gtg gct cac cgc atc ccc tgc cgg gac atg ccc ccc aca ctc        971
Ser Ala Val Ala His Arg Ile Pro Cys Arg Asp Met Pro Pro Thr Leu
130                 135                 140                 145 atc cgc acc aac cgc ttc acg gcc agc ttc cag ggc atc gtg gat gcc       1019
Ile Arg Thr Asn Arg Phe Thr Ala Ser Phe Gln Gly Ile Val Asp Ala
                150                 155                 160 tac ggc gtg ggc cgc tac cag gag gtc aac ccc gct ccc tac acc atc       1067
Tyr Gly Val Gly Arg Tyr Gln Glu Val Asn Pro Ala Pro Tyr Thr Ile
            165                 170                 175 atc acc ttc ccc ttc ctg ttt gct gtg atg ttc ggg gat gtg ggc cac       1115
Ile Thr Phe Pro Phe Leu Phe Ala Val Met Phe Gly Asp Val Gly His
        180                 185                 190 ggg ctg ctc atg ttc ctc ttc gcc ctg gcc atg gtc ctt gcg gag aac       1163
Gly Leu Leu Met Phe Leu Phe Ala Leu Ala Met Val Leu Ala Glu Asn
    195                 200                 205 cga ccg gct gtg aag gcc gcg cag aac gag atc tgg cag act ttc ttc       1211
Arg Pro Ala Val Lys Ala Ala Gln Asn Glu Ile Trp Gln Thr Phe Phe
210                 215                 220                 225 agg ggc cgc tac ctg ctc ctg ctt atg ggc ctg ttc tcc atc tac acc       1259
Arg Gly Arg Tyr Leu Leu Leu Leu Met Gly Leu Phe Ser Ile Tyr Thr
                230                 235                 240 ggc ttc atc tac aac gag tgc ttc agt cgc gcc acc agc atc ttc ccc       1307
Gly Phe Ile Tyr Asn Glu Cys Phe Ser Arg Ala Thr Ser Ile Phe Pro
            245                 250                 255 tcg ggc tgg agt gtg gcc gcc atg gcc aac cag tct ggc tgg agt gat       1355
Ser Gly Trp Ser Val Ala Ala Met Ala Asn Gln Ser Gly Trp Ser Asp
        260                 265                 270 gca ttc ctg gcc cag cac acg atg ctt acc ctg gat ccc aac gtc acc       1403
Ala Phe Leu Ala Gln His Thr Met Leu Thr Leu Asp Pro Asn Val Thr
    275                 280                 285 ggt gtc ttc ctg gga ccc tac ccc ttt ggc atc gat cct att tgg agc       1451
Gly Val Phe Leu Gly Pro Tyr Pro Phe Gly Ile Asp Pro Ile Trp Ser
290                 295                 300                 305
```

```
ctg gct gcc aac cac ttg agc ttc ctc aac tcc ttc aag atg aag atg    1499
Leu Ala Ala Asn His Leu Ser Phe Leu Asn Ser Phe Lys Met Lys Met
            310                 315                 320 tcc gtc atc ctg ggc gtc gtg cac atg gcc ttt ggg gtg gtc ctc gga    1547
Ser Val Ile Leu Gly Val Val His Met Ala Phe Gly Val Val Leu Gly
        325                 330                 335 gtc ttc aac cac gtg cac ttt ggc cag agg cac cgg ctg ctg ctg gag    1595
Val Phe Asn His Val His Phe Gly Gln Arg His Arg Leu Leu Leu Glu
    340                 345                 350 acg ctg ccg gag ctc acc ttc ctg ctg gga ctc ttc ggt tac ctc gtg    1643
Thr Leu Pro Glu Leu Thr Phe Leu Leu Gly Leu Phe Gly Tyr Leu Val
355                 360                 365 ttc cta gtc atc tac aag tgg ctg tgt gtc tgg gct gcc agg gcc gcc    1691
Phe Leu Val Ile Tyr Lys Trp Leu Cys Val Trp Ala Ala Arg Ala Ala
370                 375                 380                 385 tcg gcc ccc agc atc ctc atc cac ttc atc aac atg ttc ctc ttc tcc    1739
Ser Ala Pro Ser Ile Leu Ile His Phe Ile Asn Met Phe Leu Phe Ser
            390                 395                 400 cac agc ccc agc aac agg ctg ctc tac ccc cgg cag gag gtg gtc cag    1787
His Ser Pro Ser Asn Arg Leu Leu Tyr Pro Arg Gln Glu Val Val Gln
        405                 410                 415 gcc acg ctg gtg gtc ctg gcc ttg gcc atg gtg ccc atc ctg ctg ctt    1835
Ala Thr Leu Val Val Leu Ala Leu Ala Met Val Pro Ile Leu Leu Leu
    420                 425                 430 ggc aca ccc ctg cac ctg ctg cac cgc cac cgc cgc cgc ctg cgg agg    1883
Gly Thr Pro Leu His Leu Leu His Arg His Arg Arg Arg Leu Arg Arg
435                 440                 445 agg ccc gct gac cga cag gag gaa aac aag gcc ggg ttg ctg gac ctg    1931
Arg Pro Ala Asp Arg Gln Glu Glu Asn Lys Ala Gly Leu Leu Asp Leu
450                 455                 460                 465 cct gac gca tct gtg aat ggc tgg agc tcc gat gag gaa aag gca ggg    1979
Pro Asp Ala Ser Val Asn Gly Trp Ser Ser Asp Glu Glu Lys Ala Gly
            470                 475                 480 ggc ctg gat gat gaa gag gag gcc gag ctc gtc ccc tcc gag gtg ctc    2027
Gly Leu Asp Asp Glu Glu Glu Ala Glu Leu Val Pro Ser Glu Val Leu
        485                 490                 495 atg cac cag gcc atc cac acc atc gag ttc tgc ctg ggc tgc gtc tcc    2075
Met His Gln Ala Ile His Thr Ile Glu Phe Cys Leu Gly Cys Val Ser
    500                 505                 510 aac acc gcc tcc tac ctg cgc ctg tgg gcc ctg agc ctg gcc cac gcc    2123
Asn Thr Ala Ser Tyr Leu Arg Leu Trp Ala Leu Ser Leu Ala His Ala
515                 520                 525 cag ctg tcc gag gtt ctg tgg gcc atg gtg atg cgc ata ggc ctg ggc    2171
Gln Leu Ser Glu Val Leu Trp Ala Met Val Met Arg Ile Gly Leu Gly
530                 535                 540                 545 ctg ggc cgg gag gtg ggc gtg gcg gct gtg gtg ctg gtc ccc atc ttt    2219
Leu Gly Arg Glu Val Gly Val Ala Ala Val Val Leu Val Pro Ile Phe
            550                 555                 560 gcc gcc ttt gcc gtg atg acc gtg gct atc ctg ctg gtg atg gag gga    2267
Ala Ala Phe Ala Val Met Thr Val Ala Ile Leu Leu Val Met Glu Gly
        565                 570                 575 ctc tca gcc ttc ctg cac gcc ctg cgg ctg cac tgg gtg gaa ttc cag    2315
Leu Ser Ala Phe Leu His Ala Leu Arg Leu His Trp Val Glu Phe Gln
    580                 585                 590 aac aag ttc tac tca ggc acg ggc tac aag ctg agt ccc ttc acc ttc    2363
Asn Lys Phe Tyr Ser Gly Thr Gly Tyr Lys Leu Ser Pro Phe Thr Phe
595                 600                 605 gct gcc aca gat gac tagggcccac tgcaggtcct gccagacctc cttcctgacc    2418
Ala Ala Thr Asp Asp
610
```
tctgaggcag gagaggaata aagacggtcc gccctggcaa aaaaaaaaaa aaaaaaaaaa    2478
aaaaaaaaaa    2488

<210> SEQ ID NO 2
<211> LENGTH: 614
<212> TYPE: PRT
<213> ORGANISM: Homo sapiens

<400> SEQUENCE: 2

Met Thr Phe Leu Ile Ser Tyr Trp Gly Glu Gln Ile Gly Gln Lys Ile
1               5                   10                  15

Arg Lys Ile Thr Asp Cys Phe His Cys His Val Phe Pro Phe Leu Gln
            20                  25                  30

Gln Glu Glu Ala Arg Leu Gly Leu Gln Gln Leu Gln Gln Ser
        35                  40                  45

Gln Glu Leu Gln Glu Val Leu Gly Glu Thr Arg Phe Leu Ser Gln
    50                  55                  60

Val Leu Gly Arg Val Leu Gln Leu Leu Pro Pro Gly Gln Val Gln Val
65                  70                  75                  80

His Lys Met Lys Ala Val Tyr Leu Ala Leu Asn Gln Cys Ser Val Ser
                85                  90                  95

Thr Thr His Lys Cys Leu Ile Ala Glu Ala Trp Cys Ser Val Arg Asp
            100                 105                 110

Leu Pro Ala Leu Gln Glu Ala Leu Arg Asp Ser Ser Met Glu Glu Gly
        115                 120                 125

Val Ser Ala Val Ala His Arg Ile Pro Cys Arg Asp Met Pro Pro Thr
    130                 135                 140

Leu Ile Arg Thr Asn Arg Phe Thr Ala Ser Phe Gln Gly Ile Val Asp
145                 150                 155                 160

Ala Tyr Gly Val Gly Arg Tyr Gln Glu Val Asn Pro Ala Pro Tyr Thr
                165                 170                 175

Ile Ile Thr Phe Pro Phe Leu Phe Ala Val Met Phe Gly Asp Val Gly
            180                 185                 190

His Gly Leu Leu Met Phe Leu Phe Ala Leu Ala Met Val Leu Ala Glu
        195                 200                 205

Asn Arg Pro Ala Val Lys Ala Ala Gln Asn Glu Ile Trp Gln Thr Phe
    210                 215                 220

Phe Arg Gly Arg Tyr Leu Leu Leu Leu Met Gly Leu Phe Ser Ile Tyr
225                 230                 235                 240

Thr Gly Phe Ile Tyr Asn Glu Cys Phe Ser Arg Ala Thr Ser Ile Phe
                245                 250                 255

Pro Ser Gly Trp Ser Val Ala Ala Met Ala Asn Gln Ser Gly Trp Ser
            260                 265                 270

Asp Ala Phe Leu Ala Gln His Thr Met Leu Thr Leu Asp Pro Asn Val
        275                 280                 285

Thr Gly Val Phe Leu Gly Pro Tyr Pro Phe Gly Ile Asp Pro Ile Trp
    290                 295                 300

Ser Leu Ala Ala Asn His Leu Ser Phe Leu Asn Ser Phe Lys Met Lys
305                 310                 315                 320

Met Ser Val Ile Leu Gly Val Val His Met Ala Phe Gly Val Val Leu
                325                 330                 335

Gly Val Phe Asn His Val His Phe Gly Gln Arg His Arg Leu Leu Leu
            340                 345                 350

```
Glu Thr Leu Pro Glu Leu Thr Phe Leu Leu Gly Leu Phe Gly Tyr Leu
        355                 360                 365

Val Phe Leu Val Ile Tyr Lys Trp Leu Cys Val Trp Ala Ala Arg Ala
    370                 375                 380

Ala Ser Ala Pro Ser Ile Leu Ile His Phe Ile Asn Met Phe Leu Phe
385                 390                 395                 400

Ser His Ser Pro Ser Asn Arg Leu Leu Tyr Pro Arg Gln Glu Val Val
                405                 410                 415

Gln Ala Thr Leu Val Val Leu Ala Leu Ala Met Val Pro Ile Leu Leu
            420                 425                 430

Leu Gly Thr Pro Leu His Leu Leu His Arg His Arg Arg Leu Arg
        435                 440                 445

Arg Arg Pro Ala Asp Arg Gln Glu Glu Asn Lys Ala Gly Leu Leu Asp
        450                 455                 460

Leu Pro Asp Ala Ser Val Asn Gly Trp Ser Ser Asp Glu Glu Lys Ala
465                 470                 475                 480

Gly Gly Leu Asp Asp Glu Glu Ala Glu Leu Val Pro Ser Glu Val
                485                 490                 495

Leu Met His Gln Ala Ile His Thr Ile Glu Phe Cys Leu Gly Cys Val
            500                 505                 510

Ser Asn Thr Ala Ser Tyr Leu Arg Leu Trp Ala Leu Ser Leu Ala His
        515                 520                 525

Ala Gln Leu Ser Glu Val Leu Trp Ala Met Val Met Arg Ile Gly Leu
        530                 535                 540

Gly Leu Gly Arg Glu Val Gly Val Ala Ala Val Leu Val Pro Ile
545                 550                 555                 560

Phe Ala Ala Phe Ala Val Met Thr Val Ala Ile Leu Leu Val Met Glu
                565                 570                 575

Gly Leu Ser Ala Phe Leu His Ala Leu Arg Leu His Trp Val Glu Phe
            580                 585                 590

Gln Asn Lys Phe Tyr Ser Gly Thr Gly Tyr Lys Leu Ser Pro Phe Thr
        595                 600                 605

Phe Ala Ala Thr Asp Asp
    610

<210> SEQ ID NO 3
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 3

Arg Arg Pro Ala Asp Arg Gln Glu Glu Asn Lys Ala Gly
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic oligopeptide

<400> SEQUENCE: 4

Ser Ser Asp Glu Glu Lys Ala Gly Gly Leu Asp Asp Glu Glu
1               5                   10

<210> SEQ ID NO 5
```

```
<211> LENGTH: 14
<212> TYPE: PRT
<213> ORGANISM: Artificial sequence
<220> FEATURE:
<223> OTHER INFORMATION: Synthetic oligopeptide

<400> SEQUENCE: 5

Val Glu Phe Gln Asn Lys Phe Tyr Ser Gly Thr Gly Tyr Lys
1               5                   10

<210> SEQ ID NO 6
<211> LENGTH: 16
<212> TYPE: PRT
<213> ORGANISM: Artificial sequence
<220> FEATURE:
<223> OTHER INFORMATION: Synthetic oligopeptide

<400> SEQUENCE: 6

Ser Gly Thr Gly Tyr Lys Leu Ser Pro Phe Thr Phe Ala Ala Thr Asp
1               5                   10                  15

<210> SEQ ID NO 7
<211> LENGTH: 14
<212> TYPE: PRT
<213> ORGANISM: Artificial sequence
<220> FEATURE:
<223> OTHER INFORMATION: Synthetic oligopeptide

<400> SEQUENCE: 7

Asp Leu Pro Asp Ala Ser Val Asn Gly Trp Ser Ser Asp Glu
1               5                   10

<210> SEQ ID NO 8
<211> LENGTH: 15
<212> TYPE: PRT
<213> ORGANISM: Artificial sequence
<220> FEATURE:
<223> OTHER INFORMATION: Synthetic oligopeptide

<400> SEQUENCE: 8

Gln Glu Ala Leu Arg Asp Ser Ser Met Glu Glu Gly Val Ser Ala
1               5                   10                  15

<210> SEQ ID NO 9
<211> LENGTH: 14
<212> TYPE: PRT
<213> ORGANISM: Artificial sequence
<220> FEATURE:
<223> OTHER INFORMATION: Synthetic oligopeptide

<400> SEQUENCE: 9

Ala Asn Gln Ser Gly Trp Ser Asp Ala Phe Leu Ala Gln His
1               5                   10

<210> SEQ ID NO 10
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 10
gacggaacag cttc                                                       14

<210> SEQ ID NO 11
<211> LENGTH: 13
<212> TYPE: DNA
```

-continued

```
<213> ORGANISM: Artificial sequence
<220> FEATURE:
<223> OTHER INFORMATION: Synthetic oligonucleotide

<400> SEQUENCE: 11
tgcgtctggt tct                                                        13

<210> SEQ ID NO 12
<211> LENGTH: 2488
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (537)..(2378)
<223> OTHER INFORMATION: Synthetic construct

<400> SEQUENCE: 12
ggacgcccct gctccaggcc cccgggggggc cgcaccagga cctgagggtc aagtgagtga     60
gggatgacct catgcccttt ctggccagcc cagaaccct ggccagtcgc tgggctgggc      120
caggctgagc tccgactcct tgtccagtgc tctcccagg ctggcccgc ctcctccttc       180 aggcccggaa cttcccacag tcccaagccc tagccctagg gggttctcct cttctggtcc     240
tgcccgggag gcctcctgcc ttccctgtg ggcagggca gtgtgcccaa ttgcccgatt       300
gcccgtgctg ggcagggtcc tgcccggggg gcctggtggg ggaggcaggg caggaggttg     360
gagcagccct gcccagcccc gtggccgcca gctttgtggc aggtgccgtg gagccccaca     420
aggcccctgc cctagagcgc ctgctctgga gggcctgccg cggcttcctc attgccagct    480
tcagggagct ggagcagccg ctggagcacc ccgtgacggg cgagccagcc acgtgg atg     539
                                                                Met
                                                                  1 acc ttc ctc atc tcc tac tgg ggt gag cag atc gga cag aag atc cgc      587
Thr Phe Leu Ile Ser Tyr Trp Gly Glu Gln Ile Gly Gln Lys Ile Arg
          5                  10                  15 aag atc acg gac tgc ttc cac tgc cac gtc ttc ccg ttt ctg cag cag      635
Lys Ile Thr Asp Cys Phe His Cys His Val Phe Pro Phe Leu Gln Gln
     20                  25                  30 gag gag gcc cgc ctc ggg gcc ctg cag cag ctg caa cag cag agc cag      683
Glu Glu Ala Arg Leu Gly Ala Leu Gln Gln Leu Gln Gln Gln Ser Gln
 35                  40                  45 gag ctg cag gag gtc ctc ggg gag aca gag cgg ttc ctg agc cag gtg      731
Glu Leu Gln Glu Val Leu Gly Glu Thr Glu Arg Phe Leu Ser Gln Val
 50                  55                  60                  65 cta ggc cgg gtg ctg cag ctg ctg ccg cca ggg cag gtg cag gtc cac      779
Leu Gly Arg Val Leu Gln Leu Leu Pro Pro Gly Gln Val Gln Val His
             70                  75                  80 aag atg aag gcc gtg tac ctg gcc ctg aac cag tgc agc gtg agc acc      827
Lys Met Lys Ala Val Tyr Leu Ala Leu Asn Gln Cys Ser Val Ser Thr
         85                  90                  95 acg cac aag tgc ctc att gcc gag gcc tgg tgc tct gtg cga gac ctg      875
Thr His Lys Cys Leu Ile Ala Glu Ala Trp Cys Ser Val Arg Asp Leu
    100                 105                 110 ccc gcc ctg cag gag gcc ctg cag gac agc tcg atg gag gag gga gtg      923
Pro Ala Leu Gln Glu Ala Leu Gln Asp Ser Ser Met Glu Glu Gly Val
    115                 120                 125 agt gcc gtg gct cac cgc atc ccc tgc cgg gac atg ccc cca aca ctc      971
Ser Ala Val Ala His Arg Ile Pro Cys Arg Asp Met Pro Pro Thr Leu
130                 135                 140                 145 atc cgc acc aac cgc ttc acg gcc agc ttc cag ggc atc gtg gat gcc     1019
```

```
              Ile Arg Thr Asn Arg Phe Thr Ala Ser Phe Gln Gly Ile Val Asp Ala
                              150                 155                 160 tac ggc gtg ggc cgc tac cag gag gtc aac ccc gct ccc tac acc atc              1067
Tyr Gly Val Gly Arg Tyr Gln Glu Val Asn Pro Ala Pro Tyr Thr Ile
            165                 170                 175 atc acc ttc ccc ttc ctg ttt gct gtg atg ttc ggg gat gtg ggc cac              1115
Ile Thr Phe Pro Phe Leu Phe Ala Val Met Phe Gly Asp Val Gly His
        180                 185                 190 ggg ctg ctc atg ttc ctc ttc gcc ctg gcc atg gtc ctt gcg gag aac              1163
Gly Leu Leu Met Phe Leu Phe Ala Leu Ala Met Val Leu Ala Glu Asn
    195                 200                 205 cga ccg gct gtg aag gcc gcg cag aac gag atc tgg cag act ttc ttc              1211
Arg Pro Ala Val Lys Ala Ala Gln Asn Glu Ile Trp Gln Thr Phe Phe
210                 215                 220                 225 agg ggc cgc tac ctg ctc ctg ctt atg ggc ctg ttc tcc atc tac acc              1259
Arg Gly Arg Tyr Leu Leu Leu Leu Met Gly Leu Phe Ser Ile Tyr Thr
                230                 235                 240 ggc ttc atc tac aac gag tgc ttc agt cgc gcc acc agc atc ttc ccc              1307
Gly Phe Ile Tyr Asn Glu Cys Phe Ser Arg Ala Thr Ser Ile Phe Pro
            245                 250                 255 tcg ggc tgg agt gtg gcc gcc atg gcc aac cag tct ggc tgg agt gat              1355
Ser Gly Trp Ser Val Ala Ala Met Ala Asn Gln Ser Gly Trp Ser Asp
        260                 265                 270 gca ttc ctg gcc cag cac acg atg ctt acc ctg gat ccc aac gtc acc              1403
Ala Phe Leu Ala Gln His Thr Met Leu Thr Leu Asp Pro Asn Val Thr
    275                 280                 285 ggt gtc ttc ctg gga ccc tac ccc ttt ggc atc gat cct att tgg agc              1451
Gly Val Phe Leu Gly Pro Tyr Pro Phe Gly Ile Asp Pro Ile Trp Ser
290                 295                 300                 305 ctg gct gcc aac cac ttg agc ttc ctc aac tcc ttc aag atg aag atg              1499
Leu Ala Ala Asn His Leu Ser Phe Leu Asn Ser Phe Lys Met Lys Met
                310                 315                 320 tcc gtc atc ctg ggc gtc gtg cac atg gcc ttt ggg gtg gtc ctc gga              1547
Ser Val Ile Leu Gly Val Val His Met Ala Phe Gly Val Val Leu Gly
            325                 330                 335 gtc ttc aac cac gtg cac ttt ggc cag agg cac cgg ctg ctg ctg gag              1595
Val Phe Asn His Val His Phe Gly Gln Arg His Arg Leu Leu Leu Glu
        340                 345                 350 acg ctg ccg gag ctc acc ttc ctg ctg gga ctc ttc ggt tac ctc gtg              1643
Thr Leu Pro Glu Leu Thr Phe Leu Leu Gly Leu Phe Gly Tyr Leu Val
    355                 360                 365 ttc cta gtc atc tac aag tgg ctg tgt gtc tgg gct gcc agg gcc gcc              1691
Phe Leu Val Ile Tyr Lys Trp Leu Cys Val Trp Ala Ala Arg Ala Ala
370                 375                 380                 385 tcg gcc ccc agc atc ctc atc cac ttc atc aac atg ttc ctc ttc tcc              1739
Ser Ala Pro Ser Ile Leu Ile His Phe Ile Asn Met Phe Leu Phe Ser
                390                 395                 400 cac agc ccc agc aac agg ctg ctc tac ccc cgg cag gag gtg gtc cag              1787
His Ser Pro Ser Asn Arg Leu Leu Tyr Pro Arg Gln Glu Val Val Gln
            405                 410                 415 gcc acg ctg gtg gtc ctg gcc ttg gcc atg gtg ccc atc ctg ctg ctt              1835
Ala Thr Leu Val Val Leu Ala Leu Ala Met Val Pro Ile Leu Leu Leu
        420                 425                 430 ggc aca ccc ctg cac ctg ctg cac cgc cac cgc cgc ctg cgg agg              1883
Gly Thr Pro Leu His Leu Leu His Arg His Arg Arg Leu Arg Arg
    435                 440                 445 agg ccc gct gac cga cag gag gaa aac aag gcc ggg ttg ctg gac ctg              1931
Arg Pro Ala Asp Arg Gln Glu Glu Asn Lys Ala Gly Leu Leu Asp Leu
450                 455                 460                 465
```

-continued

| | | |
|---|---|---|
| cct gac gca tct gtg aat ggc tgg agc tcc gat gag gaa aag gca ggg<br>Pro Asp Ala Ser Val Asn Gly Trp Ser Ser Asp Glu Glu Lys Ala Gly<br>470 475 480 | 1979 | |
| ggc ctg gat gat gaa gag gag gcc gag ctc gtc ccc tcc gag gtg ctc<br>Gly Leu Asp Asp Glu Glu Glu Ala Glu Leu Val Pro Ser Glu Val Leu<br>485 490 495 | 2027 | |
| atg cac cag gcc atc cac acc atc gag ttc tgc ctg ggc tgc gtc tcc<br>Met His Gln Ala Ile His Thr Ile Glu Phe Cys Leu Gly Cys Val Ser<br>500 505 510 | 2075 | |
| aac acc gcc tcc tac ctg cgc ctg tgg gcc ctg agc ctg gcc cac gcc<br>Asn Thr Ala Ser Tyr Leu Arg Leu Trp Ala Leu Ser Leu Ala His Ala<br>515 520 525 | 2123 | |
| cag ctg tcc gag gtt ctg tgg gcc atg gtg atg cgc ata ggc ctg ggc<br>Gln Leu Ser Glu Val Leu Trp Ala Met Val Met Arg Ile Gly Leu Gly<br>530 535 540 545 | 2171 | |
| ctg ggc cgg gag gtg ggc gtg gcg gct gtg gtg ctg gtc ccc atc ttt<br>Leu Gly Arg Glu Val Gly Val Ala Ala Val Val Leu Val Pro Ile Phe<br>550 555 560 | 2219 | |
| gcc gcc ttt gcc gtg atg acc gtg gct atc ctg ctg gtg atg gag gga<br>Ala Ala Phe Ala Val Met Thr Val Ala Ile Leu Leu Val Met Glu Gly<br>565 570 575 | 2267 | |
| ctc tca gcc ttc ctg cac gcc ctg cgg ctg cac tgg gtg gaa ttc cag<br>Leu Ser Ala Phe Leu His Ala Leu Arg Leu His Trp Val Glu Phe Gln<br>580 585 590 | 2315 | |
| aac aag ttc tac tca ggc acg ggc tac aag ctg agt ccc ttc acc ttc<br>Asn Lys Phe Tyr Ser Gly Thr Gly Tyr Lys Leu Ser Pro Phe Thr Phe<br>595 600 605 | 2363 | |
| gct gcc aca gat gac tagggcccac tgcaggtcct gccagacctc cttcctgacc<br>Ala Ala Thr Asp Asp<br>610 | 2418 | |
| tctgaggcag gagaggaata aagacggtcc gccctggcaa aaaaaaaaaa aaaaaaaaa | 2478 | |
| aaaaaaaaaa | 2488 | |

<210> SEQ ID NO 13
<211> LENGTH: 614
<212> TYPE: PRT
<213> ORGANISM: Artificial sequence
<220> FEATURE:
<223> OTHER INFORMATION: Synthetic Construct

<400> SEQUENCE: 13

Met Thr Phe Leu Ile Ser Tyr Trp Gly Glu Gln Ile Gly Gln Lys Ile
1               5                   10                  15

Arg Lys Ile Thr Asp Cys Phe His Cys His Val Phe Pro Phe Leu Gln
            20                  25                  30

Gln Glu Glu Ala Arg Leu Gly Ala Leu Gln Gln Leu Gln Gln Gln Ser
        35                  40                  45

Gln Glu Leu Gln Glu Val Leu Gly Glu Thr Glu Arg Phe Leu Ser Gln
    50                  55                  60

Val Leu Gly Arg Val Leu Gln Leu Leu Pro Pro Gly Gln Val Gln Val
65                  70                  75                  80

His Lys Met Lys Ala Val Tyr Leu Ala Leu Asn Gln Cys Ser Val Ser
                85                  90                  95

Thr Thr His Lys Cys Leu Ile Ala Glu Ala Trp Cys Ser Val Arg Asp
            100                 105                 110

Leu Pro Ala Leu Gln Glu Ala Leu Gln Asp Ser Ser Met Glu Glu Gly
        115                 120                 125

Val Ser Ala Val Ala His Arg Ile Pro Cys Arg Asp Met Pro Pro Thr

-continued

```
            130                 135                 140
Leu Ile Arg Thr Asn Arg Phe Thr Ala Ser Phe Gln Gly Ile Val Asp
145                 150                 155                 160

Ala Tyr Gly Val Gly Arg Tyr Gln Glu Val Asn Pro Ala Pro Tyr Thr
                165                 170                 175

Ile Ile Thr Phe Pro Phe Leu Phe Ala Val Met Phe Gly Asp Val Gly
            180                 185                 190

His Gly Leu Leu Met Phe Leu Phe Ala Leu Ala Met Val Leu Ala Glu
        195                 200                 205

Asn Arg Pro Ala Val Lys Ala Ala Gln Asn Glu Ile Trp Gln Thr Phe
    210                 215                 220

Phe Arg Gly Arg Tyr Leu Leu Leu Leu Met Gly Leu Phe Ser Ile Tyr
225                 230                 235                 240

Thr Gly Phe Ile Tyr Asn Glu Cys Phe Ser Arg Ala Thr Ser Ile Phe
                245                 250                 255

Pro Ser Gly Trp Ser Val Ala Ala Met Ala Asn Gln Ser Gly Trp Ser
            260                 265                 270

Asp Ala Phe Leu Ala Gln His Thr Met Leu Thr Leu Asp Pro Asn Val
        275                 280                 285

Thr Gly Val Phe Leu Gly Pro Tyr Pro Phe Gly Ile Asp Pro Ile Trp
    290                 295                 300

Ser Leu Ala Ala Asn His Leu Ser Phe Leu Asn Ser Phe Lys Met Lys
305                 310                 315                 320

Met Ser Val Ile Leu Gly Val Val His Met Ala Phe Gly Val Val Leu
                325                 330                 335

Gly Val Phe Asn His Val His Phe Gly Gln Arg His Arg Leu Leu Leu
            340                 345                 350

Glu Thr Leu Pro Glu Leu Thr Phe Leu Leu Gly Leu Phe Gly Tyr Leu
        355                 360                 365

Val Phe Leu Val Ile Tyr Lys Trp Leu Cys Val Trp Ala Ala Arg Ala
    370                 375                 380

Ala Ser Ala Pro Ser Ile Leu Ile His Phe Ile Asn Met Phe Leu Phe
385                 390                 395                 400

Ser His Ser Pro Ser Asn Arg Leu Leu Tyr Pro Arg Gln Glu Val Val
                405                 410                 415

Gln Ala Thr Leu Val Val Leu Ala Leu Ala Met Val Pro Ile Leu Leu
            420                 425                 430

Leu Gly Thr Pro Leu His Leu Leu His Arg His Arg Arg Leu Arg
        435                 440                 445

Arg Arg Pro Ala Asp Arg Gln Glu Glu Asn Lys Ala Gly Leu Leu Asp
450                 455                 460

Leu Pro Asp Ala Ser Val Asn Gly Trp Ser Ser Asp Glu Glu Lys Ala
465                 470                 475                 480

Gly Gly Leu Asp Asp Glu Glu Glu Ala Glu Leu Val Pro Ser Glu Val
                485                 490                 495

Leu Met His Gln Ala Ile His Thr Ile Glu Phe Cys Leu Gly Cys Val
            500                 505                 510

Ser Asn Thr Ala Ser Tyr Leu Arg Leu Trp Ala Leu Ser Leu Ala His
        515                 520                 525

Ala Gln Leu Ser Glu Val Leu Trp Ala Met Val Met Arg Ile Gly Leu
    530                 535                 540

Gly Leu Gly Arg Glu Val Gly Val Ala Ala Val Val Leu Val Pro Ile
545                 550                 555                 560
```

```
Phe Ala Ala Phe Ala Val Met Thr Val Ala Ile Leu Leu Val Met Glu
                565                 570                 575

Gly Leu Ser Ala Phe Leu His Ala Leu Arg Leu His Trp Val Glu Phe
                580                 585                 590

Gln Asn Lys Phe Tyr Ser Gly Thr Gly Tyr Lys Leu Ser Pro Phe Thr
            595                 600                 605

Phe Ala Ala Thr Asp Asp
        610
```

T-CELL MEMBRANE PROTEIN (TIRC7) AND PEPTIDES DERIVED THEREFROM

This application is a continuation of U.S. Ser. No. 10/145,012, filed May 13, 2002, which is a divisional of U.S. application Ser. No. 09/510,646, filed Feb. 23, 2000, now abandoned, a continuation application of International PCT Application No. PCT/EP98/05462, filed Aug. 28, 1998, claiming priority of German Application No. 19738710.1, filed Aug. 29, 1997 and German Application No. 29802653.8, filed Feb. 12, 1998, the contents of which are hereby incorporated by reference into this application.

FIELD OF THE INVENTION

The present invention pertains generally to a T cell immune response cDNA 7 (TIRC7) encoding a novel T-cell transmembrane protein as well as peptides und polypeptides derived therefrom and antibodies recognizing said (poly)peptides. In a first aspect, the present invention relates to TIRC7 cDNA and its encoded protein. In a further aspect, the present invention relates to polynucleotides derived from said TIRC7 cDNA encoding a peptide or polypeptide being capable of inhibiting T-cell stimulation through the T-cell membrane protein (TIRC7). Furthermore, the present invention relates to vectors comprising such polynucleotides and host cells transformed therewith as well as their use in the production of the above-defined peptides or polypeptides. In addition, the present invention relates to the (poly)peptide encoded by said polynucleotides or obtainable by the method of the invention. In another important aspect the present invention relates to antibodies against said peptides and polypeptides that are capable of inhibiting T-cell stimulation through the T-cell membrane protein (TIRC7). The present invention additionally relates to pharmaceutical and diagnostic compositions comprising the aformentioned peptide, polypeptide, or antibody. Furthermore, the present invention relates to methods and uses for modulating immune responses through the novel TIRC7 membrane protein as well as to pharmaceutical compositions comprising agents which act on the TIRC7 membrane protein or its ligand. Also, the invention relates to the use of the before-described polynucleotide, vector, peptide, polypeptide, or antibody for the preparation of pharmaceutical compositions for use in organ transplantation, for the treatment of autoimmune, allergic or infectious diseases, or for treatment of tumors. Furthermore, the present invention relates to methods for modulating (antigen-specific) T cell unresponsiveness. The present invention encompasses methods for inducing, maintaining or reversing T cell unresponsiveness by inhibiting or stimulating an (unresponsive) T cell through the novel TIRC7 membrane protein.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

T cell activation is a serial process involving multiple signaling pathways and sequential changes in gene expression resulting in differentiation of T cells into distinct subpopulations, i.e. Th1 and Th2, which are distinguishable by their pattern of cytokine production and characterize the mode of the cellular immune response (Abbas et al., 1996; Crabtree, 1989). The T cell response is initiated by the interaction of the antigen-specific T cell receptor (TCR) with peptide presented by major histocompatibility complex (MHC) molecules on the surface of antigen presenting cells (APCs). Additional signals are provided by a network of receptor-ligand interactions mediated by a number of membrane proteins such as CD28/CTLA4 and B7, CD40/CD40L, LFA-1 and ICAM-1 (Lenschow et al., 1996; Linsley and Ledbetter, 1993; Xu et al., 1994, Bachmann et al., 1997; Schwartz, 1992), collectively called costimulatory signals (Perez et al., 1997). These membrane proteins can alter T cell activation in distinct ways (Bachmann et al., 1997) and regulate the immune response by the integration of positive and negative signals provided by these molecules (Bluestone, 1995; Perez et al., 1997). Many of the agents which are effective in modulating the cellular immune response either interfere with the T cell receptor (Cosimi et al., 1981), block costimulatory signaling (Larsen et al., 1996; Blazar et al., 1996; Kirk et al., 1997; Linsley et al., 1992; Turka et al., 1992) or inhibit intracellular activation signals downstream from these primary cell membrane triggers (Schreiber and Crabtree, 1992). Therapeutic prevention of T cell activation in organ transplantation and autoimmune diseases presently relies on panimmunosuppressive drugs interfering with downstream intracelullar events. Specific modulation of the T cell response remains a longstanding goal in immunological research.

SUMMARY OF THE INVENTION

The present invention relates to polynucleotides encoding a novel T-cell membrane protein. Furthermore, the present invention relates to peptides and polypeptides derived therefrom as well as to antibodies capable of inhibiting T-cell stimulation through the novel T-cell membrane protein. More particulary, the present invention relates to applications in the medical field that directly arise from the polynucleotides, peptides, (poly)peptides and antibodies of the invention. Additionally, the present invention relates to a novel method for testing activators and inhibitors of T-cell proliferation. The pharmaceutical compositions, methods and uses of the invention are useful therapeutically in situations where it is desirable to modulate (antigen-specific) immune responses, e.g., inducing and maintain (antigen-specific) T-cell unresponsiveness or restore (antigen-specific) T-cell responsiveness. For example, it may be necessary to induce or maintain T-cell unresponsiveness in a subject who has received an organ or bone marrow transplant to prevent graft rejection by inhibiting stimulation through the TIRC7 membrane protein. In addition, T-cell unresponsiveness can be maintained by blocking TIRC7 stimulation in a subject who has an autoimmune disease to alleviate symptoms of the autoimmune disease. In these cases, a TIRC7 inhibitory agent is administered to the subject in an amount and over a period of time sufficient to maintain T-cell unresponsiveness. Alternatively, T-cell unresponsiveness can be reversed in a subject bearing a tumor to stimulate a tumor specific T-cell response or in a subject receiving a vaccine to enhance the efficacy of the vaccine. For example, a cell (e.g., a tumor cell) can be modified to express a TIRC7 ligand or a TIRC7 stimulatory agent can be administered to the subject bearing a tumor or who has had a tumor surgically removed to prevent recurrence of the tumor. Additionally, antigen-specific responsiveness can be restored to anergized T-cells in vitro by stimulating the T-cells through TIRC7. Responsive T-cells generated in vitro can then be administered to a subject.

DETAILED DESCRIPTION OF THE PRESENT INVENTION

In view of the need of therapeutic means for the treatment of diseases related to immune responses of the human body, the technical problem of the invention is to provide means and methods for the modulation of T-cell responses which are particularly useful in organ transplantation and autoimmune diseases.

The solution to this technical problem is achieved by providing the embodiments characterized in the claims, namely a novel T-cell membrane protein encoded by T-cell Immune Response cDNA7 (TIRC7) is described which exhibits a central role in T-cell activation in vitro and in vivo. TIRC7 mRNA is transiently upregulated in the early phase of T-cell activation via a calcineurin-dependent pathway.

In a first set of experiments, the TIRC7 protein encoding cDNA has been cloned and characterized; see the first part of Example 1 and FIG. 1. Furthermore, said cDNA was subjected to in vitro translation and preliminary results obtained in MLR inhibition tests with the in vitro translated TIRC7 protein suggested. a putative immunosuppressive potential of said protein, see Example 2 with FIG. 5B.

A second (independent) set of experiments performed in accordance with the present invention (Examples 2 to 4), surprisingly revealed that modulation of TIRC7 membrane protein mediated signals with specific anti-TIRC7 membrane protein antibodies in vitro efficiently prevents T-cell proliferation and IL-2 secretion which is reversible by exogenous IL-2. Anti-TIRC7 membrane protein antibodies specifically inhibit Th1 subset specific cytokine expression but spare the Th2 cytokines. Administration of said antibodies in rats significantly prolongs kidney allograft survival. The latter described results obtained in accordance with the present invention provide evidence for an essential role of TIRC7 membrane protein in the early events of T cell activation. Thus, targeting of TIRC7 membrane protein and its encoding gene provides a novel therapeutic approach for modulation of the immune response.

Accordingly, the invention relates to a polynucleotide encoding a TIRC7 membrane protein or a biologically active fragment thereof comprising a DNA sequence selected from the group consisting of (i) DNA sequences comprising a nucleotide sequence the amino acid sequence depicted in SEQ ID NO. 2 or SEQ ID NO. 13 from amino acid position 1 to 614 or from amino acid position 1 to 601;

(ii) DNA sequences comprising the nucleotide sequence depicted in SEQ ID NO. 1 or SEQ ID NO. 12;

(iii) DNA sequences comprising a nucleotide sequence encoding a fragment or derivative of the protein encoded by the DNA sequence of (i) or (ii); and (iv) DNA sequences the complementary strand of which hybridizes with and which is at least 70% identical to the polynucleotide as defined in any one of (i) to (iii).

The term "TIRC7 membrane protein" as used in accordance with the present invention, denotes a protein involved in the signal transduction of T-cell activation and/or proliferation and that, preferably in a soluble form is capable of inhibiting or suppressing T-cell proliferation in response. to alloactivation in a mixed lymphocyte culture or in response to mitogens when exogeneously added to the culture. Studies which had been carried out within the scope of the present invention revealed that soluble in vitro translated TIRC7 protein is able to efficiently suppress in a dose dependent manner the proliferation of T-cells in response to alloactivation in a mixed lymphocyte culture or in response to mitogens; see Example 2, FIG. 5B.

The term "biologically active fragment thereof" refers to peptides and polypeptides that are derived from said TIRC7 membrane protein and that are capable of inhibiting T-cell proliferation as defined above.

Previously, a cDNA fragment was amplified by the Reverse Transcription Differential Display Polymerase Chain Reaction (DDRT-PCR) technique from RNA from cells stimulated in mixed lymphocyte culture (MLC). The amino acid sequence of the 350 base-pair (bp) cDNA fragment thus obtained was reported to belong to a new human (H+)-ATPase proton pump homologue differentially expressed in alloactivated lymphocytes as the amino acid sequence had substantial homology to a rat and bovine vesicular (H+)-ATPase proton pump, respectively. While the function of the molecule was not known, it was also speculated that its homology to a mouse T-cell derived immunosuppressive protein (J6B7, Lee, Molecular Immunology 27 (1990), 1137-1144) suggested that the corresponding gene may be involved in immunomodulation. A full-length cDNA clone was isolated by means of the 350 base-pair cDNA fragment from a library of activated human T-cells. However, the amino acid sequence of the newly cloned cDNA did not reveal further insights into the putative function of the encoded protein although some initial experiments concerning the expression pattern of gene supposedly corresponding to the 350 bp fragment and its encoded, in vitro translated protein were reported and gave rise to speculation. Furthermore, the attempt to clone the mouse homologue with the help of either the 350 bp fragment or the full-length cDNA failed.

Further investigations revealed, that the amino acid sequence of the cDNA fragment identified by DDRT-PCR from RNA of stimulated T-lymphocytes corresponds to a transmembrane region. Thus, it could not be ruled out that due to conserved structures and amino acid sequences of such transmembrane regions the full-length cDNA clone did not actually correspond to the fragment identified by DDRT-PCR. For example, there are 5 amino acid differences in the amino acid sequence of the TIRC7 protein compared with that of the transmembrane region encoded by the 350 bp fragment. Furthermore, since DDRT-PCR analysis of RNA from human lymphocytes identified several genes whose expression was changed with alloactivation (multi) gene families may exist of similar structure and/or function while only one or few members of those genes are actually identified by the above-described technique. Hence, the relevance of the preliminary results described above and the actual biological function of this unknown protein being without precedent were absolutely unclear.

The preliminary results were all the more questioned in view of the recent publication of Lee, Biochem. Biophys. Res. Communications 218 (1996), 813-821, wherein the cloning and characterization of a human osteoclast-specific 116 kDa proton pump subunit was reported the cDNA of which comprises a nucleotide and an amino acid sequence which is substantially identical to those of the gene cloned from activated human T-cells. Thus, it appeared as if the previous results reflected an artefact and/or were obtained due to the activity of a pseudo-gene of the gene described in Lee, supra.

In accordance with the present invention a polynucleotide with the nucleotide sequence of the coding region as depicted in SEQ ID NO: 1 has been identified encoding a protein of 614 amino acids (SEQ ID NO: 2) with a molecular weight of 75 kDA. Experiments performed in accordance with the present invention revealed that TIRC7 membrane protein is expressed in all lymphoid tissues with low expression only in thymus, bone marrow and fetal liver and is transiently up regulated in lymphocytes after stimulation of the T-cell receptor, see Example 1, FIG. 3. The TIRC7 encoding gene has been located by using the fluorescence-in situ-hybridization (FISH) method on the long arm of human chromosome 10 (13.4-13.5q) which is close to the breakpoint region of the bcl-gene associated with leukemia. The TIRC7 membrane protein is predominantly expressed on the cell membrane, consistent with a target for an external ligand; see Example 1, FIG. 4. The seven transmembrane domain structure predicts three extracellular loops and an extracellularly oriented carboxy terminus; see FIG. 2.

From the above it is evident that the nucleotide sequence depicted in SEQ ID NO. 1 encodes a novel class of T-cell membrane proteins. By the provision of this nucleotide sequence it is now possible to isolate identical or similar polynucleotides which code for proteins with the biological activity of TIRC7 from other species or organisms. Well-established approaches for the identification and isolation of such related sequences are, for example, the isolation from genomic or cDNA libraries using the complete or part of the disclosed sequence as a probe or the amplification of corresponding polynucleotides by polymerase chain reaction using specific primers. In accordance with the present invention, a further polynucleotide encoding a TIRC7 membrane protein was isolated using a nucleic acid molecule comprising the coding sequence of SEQ ID NO: 1 as a probe. The nucleotide sequence of said polynucleotide is given in SEQ ID NO: 12 encoding a protein having the amino acid sequence of SEQ ID NO: 13. The nucleotide and amino acid sequences of said TIRC7 membrane protein are substantially identical with those of the TIRC7 membrane protein encoded by SEQ ID NO: 1 except at amino acid position 121 (Arg→Gln) and, therefore, presumably represent allelic variants.

Thus, the invention also relates to polynucleotides which hybridize to the above described polynucleotides and differ at one or more positions in comparison to these as long as they encode a TIRC7 membrane protein as defined above. Such molecules comprise those which are changed, for example, by deletion(s), insertion(s), alteration(s) or any other modification known in the art in comparison to the above described polynucleotides either alone or in combination. Methods for introducing such modifications in the polynucleotides of the invention are well-known to the person skilled in the art; see, e.g., Sambrook et al. (Molecular cloning; A Laboratory Manual, Second Edition, Cold Spring Harbor Laboratory Press, Cold Spring Harbor N.Y. (1989)). The invention also relates to polynucleotides the nucleotide sequence of which differs from the nucleotide sequence of any of the above-described polynucleotides due to the degeneracy of the genetic code.

With respect to the DNA sequences characterized under (iv) above, the term "hybridizing" in this context is understood as referring to conventional hybridization conditions, preferably such as hybridization in 50% formamide/6×SSC/ 0.1% SDS/100 µg/ml ssDNA, in which temperatures for hybridization are above 37° C. and temperatures for washing in 0.1×SSC/0.1% SDS are above 55° C. Most preferably, the term "hybridizing" refers to stringent hybridization conditions, for example such as described in Sambrook, supra.

Particularly preferred are polynucleotides which share 70%, preferably at least 85%, more preferably 90-95%, and most preferably 96-99% sequence identity with one of the above-mentioned polynucleotides and have the same biological activity. Such polynucleotides also comprise those which are altered, for example by nucleotide deletion(s), insertion(s), substitution(s), addition(s), and/or recombination(s) and/or any other modification(s) known in the art either alone or in combination in comparison to the above-described polynucleotides. Methods for introducing such modifications in the nucleotide sequence of the polynucleotide of the invention are well known to the person skilled in the art. Thus, the present invention encompasses any polynucleotide that can be derived from the above described polynucleotides by way of genetic engineering and that encode upon expression a TIRC7 membrane protein or a biologically active fragment thereof.

It is also immediately evident to the person skilled in the art that regulatory sequences may be added to the polynucleotide of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62).

In a further embodiment, the invention relates to nucleic acid molecules of at least 15 nucleotides in length hybridizing specifically with a polynucleotide as described above or with a complementary strand thereof. Specific hybridization occurs preferably under stringent conditions and implies no or very little cross-hybridization with nucleotide sequences encoding no or substantially different proteins. Such nucleic acid molecules may be used as probes and/or for the control of gene expression. Nucleic acid probe technology is well known to those skilled in the art who will readily appreciate that such probes may vary in length. Preferred are nucleic acid probes of 17 to 35 nucleotides in length. Of course, it may also be appropriate to use nucleic acids of up to 100 and more nucleotides in length. The nucleic acid probes of the invention are useful for various applications. On the one hand, they may be used as PCR primers for amplification of polynucleotides according to the invention. Another application is the use as a hybridization probe to identify polynucleotides hybridizing to the polynucleotides of the invention by homology screening of genomic DNA libraries. Nucleic acid molecules according to this preferred embodiment of the invention which are complementary to a polynucleotide as described above may also be used for repression of expression of a gene comprising such a polynucleotide, for example due to an antisense or triple helix effect or for the construction of appropriate ribozymes (see, e.g., EP-B1 0 291 533, EP-A1 0 321 201, EP-A2 0 360 257) which specifically cleave the (pre)-mRNA of a gene comprising a polynucleotide of the invention. Selection of appropriate target sites and corresponding ribozymes can be done as described for example in Steinecke, Ribozymes, Methods in Cell Biology 50, Galbraith et al. eds Academic Press, Inc. (1995), 449-460. Standard methods relating to antisense technology have also been described (Melani, Cancer Res. 51 (1991), 2897-2901). Furthermore, the person skilled in the art is well aware that it is also possible to label such a nucleic acid probe with an appropriate marker for specific applications, such as for the detection of the presence of a polynucleotide of the invention in a sample derived from an organism.

The above described nucleic acid molecules may either be DNA or RNA or a hybrid thereof. Furthermore, said nucleic acid molecule may contain, for example, thioester bonds and/or nucleotide analogues, commonly used in oligonucleotide anti-sense approaches. Said modifications may be useful for the stabilization of the nucleic acid molecule against endo- and/or exonucleases in the cell. Said nucleic acid molecules may be transcribed by an appropriate vector containing a chimeric gene Which allows for the transcription of said nucleic acid molecule in the cell. Such nucleic acid molecules may further contain ribozyme sequences as described above.

In this respect, it is also to be understood that the polynucleotide of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

In a preferred embodiment said nucleic acid molecules are labeled. Methods for the detection of nucleic acids are well known in the art, e.g., Southern and northern blotting, PCR or primer extension. in another preferred embodiment said nucleic acid molecules may be used for the suppression of TIRC7 expression.

The polynucleotide of the invention encoding the above described TIRC7 membrane protein or biologically active fragments thereof may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions. Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (In-vitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the protein of the invention may follow; see, e.g., the appended examples.

In accordance with the above, the present invention relates to vectors, particularly plasmids, cosmids, viruses and bacteriophages used conventionally in genetic engineering that comprise a polynucleotide of the invention. Methods which are well known to those skilled in the art can be used to construct recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

In a still further embodiment, the present invention relates to a cell containing the polynucleotide or vector described above. Preferably, said cell is a eukaryotic, most preferably a mammalian cell if therapeutic uses of the protein are envisaged. Of course, yeast and less preferred prokaryotic, e.g., bacterial cells may serve as well, in particular if the produced protein is used as a diagnostic means.

The polynucleotide or vector of the invention which is present in the host cell may either be integrated into the genome of the host cell or it may be maintained extrachromosomally.

The term "prokaryotic" is meant to include all bacteria which can be transformed or transfected with a DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. TIRC7 proteins of the invention may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the TIRC7 protein of the invention in eukaryotic or prokaryotic hosts. In general, expression vectors containing promoter sequences which facilitate the efficient transcription of the inserted polynucleotide are used in connection with the host.

The expression vector typically contains an origin of replication, a promoter, and a terminator, as well as specific genes which are capable of providing phenotypic selection of the transformed cells. Furthermore, transgenic animals, preferably mammals, comprising cells of the invention may be used for the large scale production. of the TIRC7 protein of the invention.

Alternatively, an animal, preferably mammalian cell naturally having a polynucleotide of the invention present in its genome can be used and modified such that said cell expresses the endogenus gene corresponding to the polynucleotide of the invention under the control of an heterologous promoter. The introduction of the heterologous promoter which does not naturally control the expression of the polynucleotide of the invention can be done according to standard methods, see supra. Suitable promoter include those mentioned hereinbefore.

Thus, in a further embodiment, the present invention relates to a method for the production of a TIRC7 membrane protein or a biologically active fragment thereof comprising:
(a) culturing a host of the invention under conditions allowing for the expression of the protein; or
(b) in vitro translation of the polynucleotide of the invention; and recovering the protein produced in (a) or (b).

The transformed hosts can be grown in fermentors and. cultured according to techniques known in the art to achieve optimal cell growth. The TIRC7 protein of the invention can then be isolated from the growth medium, cellular lysates, or cellular membrane fractions. Once expressed, the protein of the present invention can be purified according to standard procedures of the art, including ammonium sulfate precipitation, affinity columns, column chromatography, gel electrophoresis and the like; see, Scopes, "Protein Purification", Springer-Verlag, N.Y. (1982). Substantially pure proteins of at least about 90 to 95% homogeneity are preferred, and 98 to 99% or more homogeneity are most preferred, for pharmaceutical uses. Once purified, partially or to homogeneity as desired, the proteins may then be used therapeutically (including extracorporeally) or in developing and performing assay procedures.

Hence, in a still further embodiment, the present invention relates to a TIRC7 membrane protein or a biologically active fragment thereof encoded by the polynucleotide of the invention or produced by a method of as described above. It will be apparent to those skilled in the art that the protein of the invention can be further coupled to other moieties as described above for, e.g., drug targeting and imaging applications. Such coupling may be conducted chemically after expression of the protein to site of attachment or the coupling product may be engineered into the protein of the invention at the DNA level. The DNAs are then expressed in a suitable host system, and the expressed proteins are collected and renatured, if necessary. Furthermore, the provision of the TIRC7 protein of the present invention enables the production of TIRC7 specific antibodies. In this respect, hybridoma technology enables production of cell lines secreting antibody to essentially any desired substance that produces an immune response. RNA encoding the light and heavy chains of the immunoglobulin can then be obtained from the cytoplasm of the hybridoma. The 5' end portion of the mRNA can be used to prepare cDNA to be inserted into an expression vector. The DNA encoding the antibody or its immunoglobulin chains can subsequently be expressed in cells, preferably mammalian cells.

Depending on the host cell, renaturation techniques may be required to attain proper conformation of the antibody. If necessary, point substitutions seeking to optimize binding may be made in the DNA using conventional cassette mutagenesis or other protein engineering methodology such as is disclosed herein.

Thus, the present invention also relates to an antibody specifically recognizing the peptide or polypeptide of the invention.

In a still further embodiment, the present invention relates to a cell that has been modified to express a TIRC7 protein or an antibody of the invention. This embodiment may be well suited for, e.g., restoring T-cell responsiveness to an antigen, in particular if the antibody of the invention capable of stimulating T-cell proliferation is expressed in a form suitable to be presented on the cell surface.

Moreover, the present invention relates to pharmaceutical compositions comprising a peptide or polypeptide being capable of inhibiting T-cell stimulation through the TIRC7 membrane protein and/or being recognized by an antibody capable of inhibiting T-cell stimulation through the TIRC7 membrane protein encoded by a fragment of the above described polynucleotides or an antibody specifically recognizing said peptide or polypeptide. The term "capable of inhibiting T-cell stimulation through TIRC7 membrane protein" denotes the ability of suppressing the proliferation of T-cells in response to alloactivation in a mixed lymphocyte culture or in response to mitogens by way of blocking or antagonizing the biological activity of the TIRC7 membrane protein herein also referred to as TIRC7 protein or TIRC7. The terms "capable of inhibiting T-cell stimulation through TIRC7 membrane protein" and "inhibiting TIRC7 activity" are used interchangeable herein.

Studies which had been carried out within the scope of the present invention surprisingly revealed that anti-TIRC7 antibodies directed against the extracellular domains, but not those recognizing predicted intracellular domains of the protein, are able to efficiently suppress the proliferation of T-cells in response to alloactivation in a mixed lymphocyte culture or in response to mitogens; see Example 2, FIG. 5. Similar results were obtained with in vitro translated soluble TIRC7 protein. The inhibitory effect of anti-TIRC7 antibodies on T-cells induced by a variety of different stimulatory pathways suggests that TIRC7 plays a central role in T cell activation. Moreover, inhibition of T cell proliferation in MLR by antibody targeting of TIRC7 suggest the existence of a ligand specifically interacting with TIRC7. Support for this hypothesis is provided by the dose-dependent inhibition of T cell proliferation in a MLR in the presence of soluble in vitro translated TIRC7 protein.

Furthermore, it could be shown in accordance with the present invention that antibody targeting of TIRC7 has a selective inhibitory effect on the Th1 lymphocyte subset, as evidenced by the inhibition of IL-2 and IFN-y, but not IL-4, cytokine production; see Example 3, FIG. 5. With anti-TIRC7 antibody treatment the cells appear to remain in an unresponsive, but functional, state since exogenous recombinant IL-2 reversed the antiproliferative effect of the anti-TIRC7 antibodies.

While the above described results hold promise that the novel TIRC7 protein, and antibodies thereto may be therapeutically useful, proof for the concept of the invention, namely the usefulness of the above described compounds for the modulation of the immune response as well as the embodiments derived therefrom and characterized hereinbelow came from further experiments performed in accordance with the present invention demonstrating the ability of an anti-TIRC7 antibody to prevent allograft rejection in the in vivo model of rat kidney transplantation; see Example 4, FIGS. 6 und 7. Moreover, it could be demonstrated in accordance with the present invention that advantageously the effects of antibody targeting of TIRC7 are quite similar to those observed by targeting of costimulatory molecules. Antibody blocking of costimulatory molecules has been shown to inhibit human T cell proliferation (Linsley et al., 1992; Walunas et al., 1994). Furthermore, interruption of CD28/B7 interaction with the soluble protein CTLA4Ig caused inhibition of T cell proliferation (Linsley et al., 1992; Lenschow et al., 1992; Larsen et al., 1996). Further analogy to the effect of TIRC7 antibody targeting is provided by CTLA4Ig selectively, blocking Th1 and sparing Th2 lymphocyte responses (Mohammed et al., 1995). It was shown, that administration of CTLA4Ig in an in vivo model of kidney allograft transplantation prolonged graft survival (Mohammed et al., 1995) which was similarly observed by TIRC7 antibody targeting in the present Examples. Although these similarities may suggest a costimulatory function, TIRC7 does not share structural or sequence homology with any of the known T cell accessory molecules. Thus, TIRC7 may participate in a distinct signaling pathway induced early in the course of T cell activation. This possibility is supported by recent reports that interference with pathways mediated by molecules other than the known costimulatory proteins can modulate the T cell response. For example, antibody targeting of the common leukocyte antigen CD45RB was shown to result in a prevention of graft rejection in mice (Lazarovits et al., 1996). Given the functional similarities between TIRC7 and the known T cell accessory molecules, it is expected that the structural novelty of TIRC7 will contribute to the understanding of distinct mechanisms in the T cell response. Moreover, the striking capacity of anti-TIRC7 antibody to significantly prolong allograft survival in vivo provide a novel approach for a selective inhibition of undesired T cell activation in human organ transplantation and autoimmune diseases.

In a preferred embodiment of the invention, said peptide or polypeptide encoded by the above described polynucleotide comprises the amino acid sequence depicted in any on of SEQ ID NOS 3 to 9. As described in the appended examples peptides comprising the above mentioned amino acid sequences, i.e. SEQ ID NOS 3-7, correspond to parts of the extracellular domain of the TIRC7 protein and can advantageously be used for the generation of antibodies that are capable of inducing T-cell unresponsiveness.

Accordingly, in a particularly preferred embodiment the pharmaceutical composition of the invention comprises a soluble form of said peptide or polypeptide. In one embodiment, a soluble form of TIRC7 or a TIRC7 ligand is a truncated form of the molecule comprising an extracellular domain of the TIRC7 or a functional portion thereof. A portion of the extracellular domain of TIRC7 which retains the ability to bind to a TIRC7 ligand can be used. Likewise, a portion of the extracellular domain of a TIRC7 ligand which retains the ability to bind to TIRC7 can be used. Another soluble form of TIRC7 or a TIRC7 ligand for use in accordance with the present invention is a fusion protein. The term "fusion protein" as used herein refers to a protein comprised of a first polypeptide from a first protein in contiguous amino acid sequence with a second polypeptide from a second protein. Fusion proteins can be made by standard recombinant DNA techniques wherein a nucleotide sequence encoding the first polypeptide is ligated in-frame to a nucleotide sequence encoding the second polypeptide, and these nucleotide sequences are expressed (e.g., using a recombinant expression vector introduced into a host cell) to produce the fusion protein. A preferred fusion protein is an immunoglobulin fusion protein which includes an extracellular domain, or functional portion of TIRC7 or a TIRC7 ligand linked to an immunoglobulin heavy chain constant region (e.g., the hinge, CH2 and CH3 regions of a human immunoglobulin such as IgG1). Immunoglobulin fusion proteins can be prepared, for example, according to the teachings of Capon, Nature 337 (1989), 525-531.

The antibody comprised in the pharmaceutical composition of the invention preferably has a specificity at least substantially identical to the binding specificity of the natural ligand of the TIRC7 protein of the invention, in particular if T-cell stimulation is desired. Such an antibody can have a binding affinity of at least $10^5 M^{-1}$, preferably not higher than $10^7 M^{-1}$ if T-cell stimulation is envisaged and advantageously up to $10^{10} M^{-1}$ in case T-cell suppression should be mediated.

In a preferred embodiment, antibody
(a) a T-cell suppressive antibody has an affinity of at least about $10^{-7}$ M, preferably at least about $10^{-9}$ M and most preferably at least about $10^{-11}$ M; and
(b) a T-cell stimulating antibody has an affinity of less than about $10^{-7}$ M, preferably less than about $10^{-6}$ M and most preferably in order of $10^{-5}$ M.

In case of bispecific antibodies where one specificity is directed to a target cell to be destroyed, e.g. a tumor cell, it is advantageous if the binding site recognizing the tumor antigen has a high affinity in order to capture the target cells to be destroyed with high efficiency. On the other hand, the binding affinity of the binding site recognizing the TIRC7 protein of the invention should be in the order of those of the natural TIRC7 ligand or of that usually found for the interaction of the T-cell costimulatory molecules with their receptor.

In a preferred embodiment of the invention, said antibody is a monoclonal antibody, a polyclonal antibody, a single chain antibody, humanized antibody, or fragment thereof that specifically binds said peptide or polypeptide also including bispecific antibody, synthetic antibody, antibody fragment, such as Fab, Fv or scFv fragments etc., or a chemically modified derivative of any of these. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be. used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735.

Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y.

The peptides, polypeptides and antibodies comprised in the pharmaceutical compositions of the present invention can comprise a further domain, said domain being linked by covalent or non-covalent bonds. The linkage can be based on genetic fusion according to the methods known in the art and described above or can be performed by, e.g., chemical cross-linking as described in, e.g., WO 94/04686. The additional domain present. in the fusion protein comprising the peptide, polypeptide or antibody employed in accordance with the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the peptide, polypeptide or antibody or vice versa. The above described fusion protein may further comprise a cleavable linker or cleavage site for proteinases.

Furthermore, said further domain may be of a predefined specificity or function. For example, the literature contains a host of references to the concept of targeting bioactive substances such as drugs, toxins, and enzymes to specific points in the body to destroy or locate malignant cells or to induce a localized drug or enzymatic effect. It has been proposed to achieve this effect by conjugating the bioactive substance to monoclonal antibodies (see, e.g., N.Y. Oxford University Press; and Ghose, (1978) J. Natl. Cancer Inst. 61:657-676).

In this context, it is understood that the polypeptides present in the pharmaceutical composition according to the invention may be further modified by conventional methods known in the art. This allows for the construction of fusion proteins comprising the peptide, polypeptide or antibody of the invention and other functional amino acid sequences, e.g., nuclear localization signals, transactivating domains, DNA-binding domains, hormone-binding domains, protein tags (GST, GFP, h-myc peptide, FLAG, HA peptide) which may be derived from heterologous proteins. Thus, administration of the composition of the invention can utilize unlabeled as well as labeled (poly)peptides or antibodies.

For example, the peptides, polypeptides and antibodies can be administered labeled with a therapeutic agent. These agents can be coupled either directly or indirectly to the antibodies or (poly)peptides of the invention, see supra, and can be selected to enable drug release from the antigen at the target site. Examples of therapeutic agents which can be coupled to the (poly)peptides and antibodies for immunotherapy are drugs, radioisotopes, lectins, and toxins. The drugs which can be conjugated to the polypeptides of the invention include compounds which are classically referred to as drugs' such as mitomycin C, daunorubicin, and vinblastine. In using radioisotopically conjugated (poly)peptides or antibodies of the invention for, e.g., immunotherapy, certain isotopes may be more preferable than others depending on such factors as leukocyte distribution as well as stability and emission. Depending on the autoimmune response, some emitters may be preferable to others. In general, $\alpha$ and $\beta$ particle-emitting radioisotopes are preferred in immunotherapy. Preferred are short range, high energy $\alpha$ emitters such as $^{212}$Bi. Examples of radioisotopes which can be bound to the (poly)peptides and antibodies of the invention for therapeutic purposes are $^{125}$I, $^{131}$I, $^{90}$Y, $^{67}$Cu, $^{212}$Bi, $^{212}$At, $^{211}$Pb, $^{47}$Sc $^{109}$Pd and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the $\alpha$-peptide chain of ricin, which is responsible for toxicity, to the polypeptide to enable site specific delivery of the toxic effect.

Toxins are poisonous substances produced by plants, animals, or microorganisms that, in sufficient dose, are often lethal. Diphtheria toxin is a substance produced by Corynebacterium diphtheria which can be used therapeutically. This toxin consists of an $\alpha$ and $\beta$ subunit which under proper conditions can be separated. The toxic A component can be bound to an antibody of the invention and be used for site specific delivery to the interacting T-cell.

Other therapeutic agents such as described above which can be coupled to the polypeptide of the invention, as well as correspoding ex vivo and in vivo therapeutic protocols, are known, or can be easily ascertained, by those of ordinary skill in the art. Wherever appropriate the person skilled in the art may use a polynucleotide of the invention described hereinbelow encoding any one of the above described (poly)peptides and antibodies, respectively, or the corresponding vectors instead of the proteinaceous material itself.

Thus, the person skilled in the art will readily appreciate that the (poly)peptide and antibody of the invention can be used for the construction of fusion proteins of desired specificity and biological function. The (poly)peptides and antibodies then optionally employed in accordance with the present invention of the invention as well as fusion protein thereof are expected to play an important therapeutic and scientific role in particular in the medical field, for example, in the development of new treatment approaches for T-cell related disorders such as certain forms of cancer and autoimmune diseases or as interesting tools for the analysis and modulation of the corresponding cellular signal transduction pathways.

Preferably said further domain comprises a molecule selected from the group consisting of effector molecules having a conformation suitable for biological activity, amino acid sequences capable of sequestering an ion, and amino acid sequences capable of selective binding to a solid support or to a preselected antigen. Said domain may comprises an enzyme, toxin, receptor, binding site, biosynthetic antibody binding site, growth factor, cell-differentiation factor, lymphokine, cytokine, hormone, a remotely detectable moiety, anti-metabolite, a radioactive atom or an antigen. Said antigen can be, e.g., tumor antigen, a viral antigen, a microbial antigen, an allergen, an auto-antigen, a virus, a microorganism, a polypeptide, a peptide or a plurality of tumor cells. Furthermore, said sequence capable of sequestering an ion includes calmodulin, methallothionein, a fragment thereof, or an amino acid sequence rich in at least one of glutamic acid, aspartic acid, lysine, and arginine. In addition, said polypeptide sequence capable of selective binding to a solid support can be a positively or negatively charged amino acid sequence, a cysteine-containing amino acid sequence, avidin, streptavidin, a fragment of Staphylococcus protein A, GST, a His-tag, a FLAG-tag, Lex A or c-myc as used in the appended examples. Some of the effector molecules and amino acid sequences described above may be present in a proform which itself is either active or not and which may be removed, when, e.g., entering a certain cellular environment.

The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as T-cell costimulatory molecules or cytokines known in the art, or their inhibitors or activators depending on the intended use of the pharmaceutical composition.

Furthermore, it is envisaged by the present invention that the various polynucleotides and vectors encoding the above described peptides or polypeptides are administered either alone or in any combination using standard vectors and/or gene delivery systems, and optionally together with a pharmaceutically acceptable carrier or excipient. For example, the polynucleotide of the invention can be used alone or as part of a vector to express the (poly)peptide of the invention in cells, for, e.g., gene therapy or diagnostics of diseases related to T-cell disorders. The polynucleotides or vectors of the invention are introduced into the cells which in turn produce the (poly)peptide. Subsequent to administration, said polynucleotides or vectors may be stably integrated into the genome of the subject. On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying of different kinds of diseases, which are related to T-cell related immunodeficiencies and malignancies.

Furthermore, it is possible to use a pharmaceutical composition of the invention which comprises polynucleotide or vector of the invention in gene therapy. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77.(1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell populations. Preferably, said cell is a germ line cell, embryonic cell., or egg cell or derived therefrom, most preferably said cell is a stem cell. As mentioned above, suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). It is to be understood that the introduced polynucleotides and vectors express the gene product after introduction into said cell and preferably remain in this status during the lifetime of said cell. For example, cell lines which stably express the polynucleotide under the control of appropriate regulatory sequences may be engineered according to methods well known to those skilled in the art. Rather than using expression vectors which contain viral origins of replication, host cells can be transformed with the polynucleotide of the invention and a selectable marker, either on the same or separate plasmids. Following the introduction of foreign DNA, engineered cells may be allowed to grow for 1-2 days in an enriched media, and then are switched to a selective media. The selectable marker in the recombinant plasmid confers resistance to the selection and allows for the selection of cells having stably integrated the plasmid into their chromosomes and grow to form foci which in turn can be cloned and expanded into cell lines. Such engineered cell lines are also particularly useful in screening methods for the detection of compounds involved in, e.g., T-cell activation or stimulation.

A number of selection systems may be used, including but not limited to the herpes simplex virus thymidine kinase (Wigler, Cell 11(1977), 223), hypoxanthine-guanine phosphoribosyltransferase (Szybalska, Proc. Natl. Acad. Sci. USA 48 (1962), 2026), and adenine phosphoribosyltransferase (Lowy, Cell 22 (1980), 817) in tk$^-$, hgprt$^-$ or aprt$^-$ cells, respectively. Also, antimetabolite resistance can be used as the basis of selection for dhfr, which confers resistance to methotrexate (Wigler, Proc. Natl. Acad. Sci. USA 77 (1980), 3567; O'Hare, Proc. Natl. Acad. Sci. USA 78 (1981), 1527), gpt, which confers resistance to mycophenolic acid (Mulligan, Proc. Natl. Acad. Sci. USA 78 (1981), 2072); neo, which confers resistance to the aminoglycoside G-418 (Colberre-Garapin, J. Mol. Biol. 150 (1981), 1); hygro, which confers resistance to hygromycin (Santerre, Gene 30 (1984), 147); or puromycin (pat, puromycin N-acetyl transferase). Additional selectable genes have been described, for example, trpB, which allows cells to utilize indole in place of tryptophan; hisD, which allows cells to utilize histinol in place of histidine (Hartman, Proc. Natl. Acad. Sci. USA 85 (1988), 8047); and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.).

In another embodiment the present invention relates to a diagnostic composition comprising any one of the above described proteins, antibodies, (poly)peptides, polynucleotides, vectors or cells and optionally suitable means for detection. The (poly)peptides and antibodies described above are, for example, suited for use in immunoassays in which they can be utilized in liquid phase or bound to a solid phase carrier. Examples of immunoassays which can utilize said (poly)peptide are competitive and non-competitive immunoassays in either a direct or indirect format. Examples of such immunoassays are the radioimmunoassay (RIA), the sandwich (immunometric assay) and the Western blot assay. The (poly)peptides and antibodies can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite.

The nature of the carrier can be either soluble or insoluble for the purposes of the invention.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

Said diagnostic compositions may also be used for methods for detecting expression of a polynucleotide of the invention by detecting the presence of mRNA coding for a TIRC7 membrane protein which comprises obtaining mRNA from a cell and contacting the mRNA so obtained with a probe comprising a nucleic acid molecule of at least 15 nucleotides capable of specifically hybridizing with a polynucleotide of the invention under suitable hybridizing conditions (see also supra), detecting the presence of mRNA hybridized to the probe, and thereby detecting the expression of the TIRC7 protein by the cell.

Furthermore, the invention comprises methods of detecting the presence of a TIRC7 membrane protein in a sample, for example, a cell sample, which comprises obtaining a cell sample from a subject, contacting said sample with one of the aforementioned antibodies under conditions permitting binding of the antibody to the TIRC7 protein, and detecting the presence of the antibody so bound, for example, using immuno assay techniques such as radioimmunoassay or enzymeimmunoassay. Furthermore, one skilled in the art may specifically detect and distinguish polypeptides which are functional TIRC7 proteins from mutated forms which have lost or altered their T-cell stimulatory activity by using an antibody which either specifically recognizes a (poly)peptide which has TIRC7 activity but does not recognize an inactive form thereof or which specifically recognizes an inactive form but not the corresponding polypeptide having TIRC7 activity. The antibodies of the present invention may also be used in affinity chromatography for purifying the TIRC7 membrane protein or above described (poly)peptides and isolating them from various sources.

The invention also encompasses a method for diagnosing in a subject a predisposition to a disorder associated with the expression of a TIRC7 allele which comprises isolating DNA from victims of the theg disorder associated with the under- or over-expression of a TIRC7 protein; digesting the isolated DNA with at least one restriction enzyme; electrophoretically separating the resulting DNA fragments on a sizing gel; contacting the resulting gel with a nucleic acid probe as described above capable of specifically hybridizing to DNA encoding a TIRC7 protein and labeled with a detectable marker; detecting labeled bands on the gel which have hybridized to the labeled probe to create a band pattern specific to the DNA of victims of the disorder associated with the expression of a TIRC7 protein; preparing the subject's DNA according to the above-mentioned steps to produce detectable labeled bands on a gel; and comparing the band pattern specific to the DNA of victims of the disorder associated with the expression of a TIRC7 protein and the subject's DNA to determine whether the patterns are the same or different and to diagnose thereby predisposition to the disorder if the patterns are the same. The detectable markers of the present invention may be labeled with commonly employed radioactive labels, such as, for example, $^{32}P$ and $^{35}S$, although other labels such as biotin or mercury as well as those described above may be employed as well. Various methods well-known to the person skilled in the art may be used to label the detectable markers. For example, DNA sequences and RNA sequences may be labeled with $^{32}p$ or $^{35}S$ using the random primer method. Once a suitable detectable marker has been obtained, various methods well-known to the person skilled in the art may be employed for contacting the detectable marker with the sample of interest. For example, DNA-DNA, RNA-RNA and DNA-RNA hybridizations may be performed using standard procedures. Various methods for the detection of nucleic acids are well-known in the art, e.g., Southern and northern blotting, PCR, primer extension and the like. Furthermore, the mRNA, cRNA, cDNA or genomic DNA obtained from the subject may be sequenced to identify mutations which may be characteristic fingerprints of TIRC7 mutations in disorders associated with the expression of TIRC7 or mutated versions thereof. The present invention further comprises methods, wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example. RNase $T_1$, RNase $T_2$ or the like or a ribozyme and, for example, electrophoretically separating and detecting the RNA fragments on PAGE as described above or in the appended examples.

In a preferred embodiment, the pharmaceutical composition of the present invention comprises at least one second agent, preferably an agent which inhibits or activates T-cell stimulation depending on the intended use. Such agents include, for example, molecules that are capable of blocking or mimicking receptor/ligand interaction or the like which leads to T-cell suppression and activation, respectively.

Such agents comprise those blocking the activity of, e.g., costimulatory molecules, integrins, Ig-superfamily molecules, selectins as well as drugs blocking chemokines and their respective receptor interactions, drugs blocking IL2/IL2-receptor interaction and other conventional immunosuppressive drugs such as IL-2R mAbs, IL-Toxins and IL-Muteins. Examples for costimulatory molecules and their ligands are described in the prior art, e.g., in Schwartz, Cell 71 (1992), 1065-1068. The interruption of the receptor/ligand interactions by using mAbs or soluble CTLA4Ig for the interaction between CD28 to the B7-2 and CTLA4 to B7-1 and B7-2 are described in Blazar, J. Immunol. 157 (1996), 3250-3259; Bluestone, Immunity 2 (1995), 555-559; Linsley, Science 257 (1992), 792-95. Examples for blocking the receptor/ligand interaction by using mAbs to CD40 or CD40L are reported by Burden, Nature 381 (1996), 434-435; Kirk, Proc. Natl. Acad. Sci. USA 94 (1997), 8789-8794. CD2 antigen and its ligand LFA-3 are described in Bagogui Li et al., review in Adhesion Molecules, Fusion proteins, Novel Peptides, and Monoclonal Antibodies, Recent Developments in Transplantation Medicine, Vol. II, 1995, Physicians & Scientists Publishing Co., Inc. and blocking of their interaction by using of mAbs (anti-Leu-5b, OKT11, T11) is reported in Brumberg, Transplantation 51 (1991) 219-225 or CD2.IgG1 fusion protein. The use of monoclonal Abs agains CD4 molecule is described in Cosimi, Surgery 108 (1990), 406-414. CD47 blockade by mAbs is described by Rheinhold, J. Exp. Med. 185 (1997), 1-11. Integrins and Ig-superfamily molecules include LFA-1 with its ligand ICAM-1, -2, -3, Mac-1 with ist ligand ICAM-1, -3; ICAM-1 with its ligand LFA-1, Mac-1, CD43; ICAM-2 with ist ligand LFA-1; ICAM-3 with its ligand LFA-1, Mac-1; VLA4 and VCAM-1 see, e.g., David, Adams, review in Adhesion Molecules, Fusion proteins, Novel Peptides, and Monoclonal Antibodies, Recent Developments in Transplantation Medicine, Vol. 11, 1995, Physicians & Scientists Publishing Co., Inc.; Isobe, Science, 255 (1992), 1125-1127; Cosimi, J. Immunology 144 (1990), 4604-4612; Hynes, Cell 69 (1992),11-25. Furthermore selectively interfering agents with VLA-4 mAbs to the alpha4 integrin chain (CD49d) can be used, beta1 integrin chain (CD29), or an activation—induced neo-epitope of VLA-4 as well as soluble VLA-4 ligands such as soluble fibronectin or its relevant peptide (GPEILDVPST), or soluble VCAM-1 or its relevant peptide. More selectively blocking agents are antisense oligonucleotides, designed to selectively hybridize with cytoplasmic alpha4, beta1, or VCAM-1 mRNA; Fedoseyeva, J. Immunol. 57 (1994), 606-612.

Another example is the drug pentoxifylline (PTX) that is able to block expression of VCAM-1; Besler, J. Leukoc. Biol. 40 (1986), 747-754. Furthermore, VCAM-1 mAb, M/K-2, anti-murine, for example could prolong allograft survival, Orosz, Transplantation, 56 (1993), 453-460.

Blocking of members of the integrin family and their ligands by using mAbs is decribed in Kupiec-Weglinski, review in Adhesion Molecules, Fusion proteins, Novel Peptides, and Monoclonal Antibodies, Recent Developments in Transplantation Medicine, Vol. 11, 1995, Physicians & Scientists Publishing Co., Inc. Selectins, e.g., L-selectin (CD62L), E-selectin (CD62E), P-selectin (CD62P) have been described in Forrest and Paulson, Selectin family of adhesion molecules. In: Granger and Schmid-Schonbein, eds. Physiology and Pathophysiology of Leukocyte Adhesion. New York, Oxford Press, 1995, pp 68-146.

The combination of conventional immunosuppressive drugs, e.g., ATG, ALG, OKT3, Azathioprine, Mycophenylate, Mofetyl, Cyclosporin A, FK506, Corticosteroids may be used as described in Cosimi, Transplantation 32 (1981), 535-539; Shield, Transplantation 38 (1984), 695-701.

The interruption of chemokines and interactions with their respective receptor by using mAbs is reviewed in Luster, Chemokines-chemotactic cytokines that mediate inflammation, New Engl. J. Med. Feb. (1998), 436-445.

Thus, any agent as defined above and referenced by way of example can be used in accordance with the pharmaceutical composition of the invention or the methods and uses described hereinbelow. On the other hand, it is evident to the person skilled in the art that the polynucleotides, vectors, proteins, peptides, polypeptides, antibodies, cells, and pharmaceutical compositions of the invention can be used for methods and uses described for the above referenced T-cell costimulatory molecules, inhibitors and drugs.

Advantageously, the pharmaceutical composition of the invention is intended for use in organ transplantation, for the treatment of autoimmune, allergic or infectious diseases, or for the treatment of tumors. An example for the use of the pharmaceutical composition of the invention for improving allograft or xenograft tolerance is described with respect to administration of an LFA-3 and CD2 binding protein, respectively, in WO93/06852.

Furthermore, this invention pertains to methods for modulating (antigen-specific) T-cell unresponsiveness. The term "T-cell unresponsiveness" as used herein refers to a reduction in or lack of T-cell proliferation, lymphokine secretion or induction of effector functions by a T-cell upon exposure to the antigen (or antigenic portion). The pharmaceutical compositions of this invention provide a means for inducing, maintaining or reversing unresponsiveness of a T-cell to an antigen in vitro or in vivo. Accordingly, the compounds of this invention are particularly useful for modulating (antigen-specific) T-cell unresponsiveness. The term "modulation" is intended to include both inducing and maintenance of an unresponsive state and reversal of an unresponsive state, i.e., restoration of T-cell responsiveness.

As is described in Example 3, after anti-TIRC7 antibody treatment T-cells remain in an unresponsive, but functional state since exogenous recombinant IL-2 reversed the antiproliferative effect of the antibodies. Thus, in another embodiment the present invention relates to an in vitro method for inducing or maintaining unresponsiveness of a T-cell to an antigen comprising contacting the T-cell with an agent which inhibits stimulation of the T-cell through a TIRC7 membrane protein. Recipes for how to carry out methods for modulation T-cell unresponsiveness are generally known to the skilled person and are described in, e.g., WO95/24217 and references cited therein.

Hence, the present invention also relates to the use of an agent which inhibits T-cell stimulation through a TIRC7 membrane protein for the preparation of a pharmaceutical composition for inducing or maintaining T-cell unresponsiveness to an antigen in a subject. The methods and uses of the invention may be used with primed or unprimed T-cells depending on what is intended by the person skilled in the art.

Preferably, in the method or the use of the invention the agent blocks an interaction of the TIRC7 membrane protein with its ligand. As is described above, the results of the experiments performed within the scope of the present invention suggest the existence of a ligand interacting with the TIRC7 protein and thereby stimulating T-cell proliferation. Blocking said interaction, e.g. with antibodies or soluble (poly)peptides derived from the TIRC7 membrane protein should result in T cell unresponsiveness. Thus, in a preferred embodiment of the method or the use of the invention the agent is a polynucleotide, a vector, a cell, peptide or polypeptide, or antibody described hereinbefore.

In another preferred embodiment of the invention, the above described method or use further comprise the use of a second agent as defined above.

In another embodiment, the present invention relates to a pharmaceutical composition comprising a first agent which stimulates a T-cell through a TIRC7 membrane protein, and optionally a pharmaceutically acceptable carrier. As is immediately evident to the person skilled in the art, the provision of the novel TIRC7 protein of the invention opens up the way of alternative approaches for T-cell stimulation and treating corresponding diseases. The agent that stimulates the T-cell through the TIRC7 membrane protein is expected to markedly enhance the proliferation of (activated) T-cells and thus is capable of augmenting the immune response. Examples for this type of "Vaccine" is described, e.g., in WO91/1 1194 and in the literature, e.g., referred to above. Such agents also comprise promoters which can be inserted in front of the coding region of the TIRC7 protein encoding gene, e.g., via gene transfer and homologous recombination in the 5' untranslated region of the gene, see also supra. Such promoter may be regulated and thus permit the controlled expression of the TIRC7 protein in certain cells.

Preferably, said agent is a ligand of the TIRC7 membrane protein or is at least one anti-TIRC7 membrane protein antibody described above.

In a preferred embodiment of the invention, the pharmaceutical composition further comprises a second agent which stimulates T-cell proliferation, for example IL-2, IL-4 or an agent which stimulates a T-cell through a CD2, CD28, CD40 or CTLA4 surface receptor.

In a further embodiment the present invention relates to an in vitro method for restoring responsiveness to an antigen by a T-cell which is unresponsive to the antigen, comprising contacting the T-cell in the presence of the antigen with a first agent which stimulates the T-cell through a TIRC7 membrane protein. Besides the application of the ligand itself said TIRC7 ligand may be preferably expressed on the cell surface by introducing into the cell a nucleic acid molecule encoding the TIRC7 ligand in a suitable form for expression of the TIRC7 ligand on the cell surface. Preferably the cell is a tumor cell. Vectors and methods for the introduction of such, nucleic acid molecules are well known to the skilled person and are also described, e.g., above.

The method of the invention can further comprise contacting the T-cell with a second agent as defined for the pharmaceutical compositions above. Preferably, the T-cell is contacted with the second agent prior to being contacted with the first agent.

In a preferred embodiment of the method of the invention, the second agent, preferably CD2, CD28, CTLA4 ligand or CD40 is expressed on the cell surface by introducing into the cell a nucleic acid molecule encoding the CD2, CD28, CTLA4 ligand or CD40 in a form suitable for expression of said ligand on the cell surface.

In another embodiment, the present invention relates to the use of a first agent as defined above, which is capable of stimulating a T-cell through a TIRC7 membrane protein for the preparation of a pharmaceutical composition for stimulating a T-cell response to a tumor cell in a subject with a tumor. Such agents comprise, for example, also bispecific antibodies described supra. Preferably the tumor cell is modified to express a TIRC7 ligand and/or a CD2, CD28, CTLA4 ligand or CD40 preferably on the tumor cell surface.

In a preferred embodiment of the use the invention the tumor cell is obtained from the subject, modified ex vivo to form a modified tumor cell and said modified tumor cell is used for the preparation of a pharmaceutical composition which is designed for administration to the subject.

In another preferred embodiment of the use of the invention the T-cells are obtained from a subject, contacted with IL-2 or IL-4 ex vivo and said modified T-cells are used for the preparation of pharmaceutical composition which is designed for the administration to the subject.

In a particularly preferred embodiment of the invention, the uses, methods and pharmaceutical compositions are intended to be applied to a subject who is a recipient of bone marrow transplant or peripheral stem cell transplant. Preferably the pharmaceutical composition is designed for contacting with bone marrow or peripheral stem cell prior to transplantation into the recipient.

In a further particular preferred embodiment, the methods and uses of the present invention are applied in organ graft transplantation, peripheral stem cell transplantation or for the treatment of auto-immune diseases or allergy.

Furthermore, the invention relates to a method for identifying T-cell activating or co-stimulating compounds or for identifying inhibitors of T-cell activation and stimulation comprising (a) culturing T-cells in the presence of the TIRC7 protein, (poly)peptide, antibody, or cell described above and, optionally, in the presence of a component capable of providing a detectable signal in response to T-cell activation, with a compound. to be screened under conditions permitting interaction of the compound with the TIRC7 protein, (poly)peptide, antibody or cell(s); and (b) detecting the presence or absence of a signal generated from the interaction of the compound with the cells.

The term "compound" in the method of the invention includes a single substance or a plurality of substances which may or may not be identical.

Said compound(s) may be comprised in, for example, samples, e.g., cell extracts from, e.g., plants, animals or microorganisms. Furthermore, said compounds may be known in the art but hitherto not known to be capable of inhibiting T-cell activation or not known to be useful as a T-cell costimulatory factor, respectively. The plurality of compounds may be, e.g., added to the culture medium or injected into the cell.

If a sample containing (a) compound(s) is identified in the method of the invention, then it is either possible to isolate the compound from the original sample identified as containing the compound, in question or one can further subdivide the original sample, for example, if it consists of a plurality of different compounds, so as to reduce the number of different substances per sample and repeat the method with the subdivisions of the original sample. It can then be determined whether said sample or compound displays the desired properties by methods known in the art such as described herein and in the appended examples. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art (see, e.g., EP-A-0 403 506) or by using and modifying the methods as described in the appended examples. Furthermore, the person skilled in the art will readily recognize which further compounds and/or cells may be used in order to perform the methods of the invention, for example, B-cells, interleukins, or enzymes, if necessary, that, e.g., convert a certain compound into the precursor which in turn stimulates or suppresses T-cell activation or that provide for (co)stimulatory signals. Such adaptation of the method of the invention is well within the skill of the person skilled in the art and can be performed without undue experimentation.

Compounds which can be used in accordance with the method of the present invention include peptides, proteins, nucleic acids including cDNA expression libraries, antibodies, small organic compounds, ligands, peptidomimetics, PNAs and the like. Said compounds can also be functional derivatives or analogues of known T-cell activators or inhibitors. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, said derivatives and analogues can be tested for their effects according to methods known in the art or as described, for example, in the appended examples. Furthermore, peptidomimetics and/or computer aided design of appropriate activators or inhibitors of T-cell activation can be used, for example, according to the methods described below. Appropriate computer programs can be used for the identification of interactive sites of a putative inhibitor and the TIRC7 protein by computer assistant searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N. Y. Acad. Sci. 501 (1987), 1-13; Pabo, Biochemistry 25 (1986), 5987-5991. The results obtained from the above-described computer analysis can be used in combination with the method of the invention for, e.g., optimizing known T-cell activators or inhibitors. Appropriate peptidomimetics can also be identified by the synthesis of peptidomimetic combinatorial libraries through successive chemical modification and testing the resulting compounds, e.g., according to the methods described herein and in the appended examples. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of inhibitors or activators of T-cell stimulation can be used for the design of peptidomimetic inhibitors or activators of T-cell activation to be tested in the method of the invention (Rose, Biochemistry 35 (1996), 12933-12944; Rutenber, Bioorg. Med. Chem. 4 (1996), 1545-1558).

In summary, the present invention provides methods for identifying compounds which are capable. of modulating T-cell mediated immune responses. Accordingly compounds identified in accordance with the method of the present invention to be inhibitors and activators, respectively, of T-cell stimulation or activation are also within the scope of the present invention.

Compounds found to activate T-cell mediated responses may be used in the treatment of cancer and related diseases. In addition, it may also be possible to specifically inhibit viral diseases, thereby preventing viral infection or viral spread. Compounds identified as suppressors of T-cell activation or stimulation can be used, e.g., for treating skin conditions (see, e.g., WO93/06866) or in allogenic or xenogenic cell or organ transplantation in order to avoid graft rejection; see also supra.

The compounds identified or obtained according to the method of the present invention are thus expected to be very useful in diagnostic and in particular for therapeutic applications.

Hence, in a further embodiment the invention relates to a method for the production of a pharmaceutical composition comprising formulating and optionally synthesizing the compound identified in step (b) of the above described method of the invention in a pharmaceutically acceptable form. Hence, the present invention generally relates to a method of making a therapeutic agent comprising synthesizing the proteins, (poly)peptides, polynucleotides, vectors, antibodies or compounds according to the invention in an amount sufficient to provide said agent in a therapeutically effective amount to the patient. Methods for synthesizing these agents are well known in the art and are described, e.g. above.

The therapeutically useful compounds identified according to the method of the invention may be administered to a patient by any appropriate method for the particular compound, e.g., orally, intravenously, parenterally, transdermally, transmucosally, or by surgery or implantation (e.g., with the compound being in the form of a solid or semi-solid biologically compatible and resorbable matrix) at or near the site where the effect of the compound is desired. Therapeutic doses are determined to be appropriate by one skilled in the art, see also supra.

Such useful compounds can be for example transacting factors which bind to the TIRC7 protein of the invention. Identification of transacting factors can be carried out using standard methods in the art (see, e.g., Sambrook, supra, and Ausubel, supra). To determine whether a protein binds to the TIRC7 protein of the invention, standard native gel-shift analyses can be carried out. In order to identify a transacting factor which binds to the TIRC7 of the invention, the polypeptides and peptides of the invention can be used as an affinity reagent in standard protein purification methods, or as a probe for screening an expression library. Once the transacting factor is identified, modulation of its binding to the TIRC7 protein of the invention can be pursued, beginning with, for example, screening for inhibitors against the binding of the transacting factor to the TIRC7 protein of the present invention. Activation or repression of TIRC7 specific genes could then be achieved in subjects by applying the transacting factor (or its inhibitor) or the gene encoding it, e.g., in a vector described in the embodiments hereinbefore. In addition, if the active form of the transacting factor is a dimer, dominant-negative mutants of the transacting factor could be made in order to inhibit its activity. Furthermore, upon identification of the transacting factor, further components in the pathway leading to activation (e.g. signal transduction) or repression of a gene encoding the TIRC7 protein of the present invention can then be identified. Modulation of the activities of these components can then be pursued, in order to develop additional drugs and methods for modulating the expression or activity of the TIRC7 protein of the present invention.

Beside the above described possibilities to use the polynucleotides according to the invention for gene therapy and their use to identify homologous molecules, the described polynucleotides may also be used for several other applications, for example, for the identification of nucleic acid molecules which encode proteins which interact with the TIRC7 protein described above. This can be achieved by assays well known in the art, for example, as described in Scofield (Science 274 (1996), 2063-2065) by use of the so-called yeast "two-hybrid system". In this system the (poly)peptide encoded by the polynucleotides according to the invention or a smaller part thereof is linked to the DNA-binding domain of the GAL4 transcription factor. A yeast strain expressing this fusion protein and comprising a lacZ reporter gene driven by an appropriate promoter, which is recognized by the GAL4 transcription factor, is transformed with a library of cDNAs which will express animal, preferably mammal proteins or peptides thereof fused to an activation domain. Thus, if a peptide encoded by one of the cDNAs is able to interact with the fusion protein comprising a (poly)peptide of the invention, the complex is able to direct expression of the reporter gene. In this way the polynucleotide according to the invention and the encoded peptide can be used to identify peptides and proteins interacting with TIRC7 proteins. Other methods for identifying compounds which interact with the TIRC7 protein according to the invention or nucleic acid molecules encoding such molecules are, for example, the in vitro screening with the phage display system as well as filter binding assays or "real time" measuring of interaction using, for example, the BIAcore apparatus (Pharmacia); see references cited supra.

Furthermore, the present invention relates to the use of the polynucleotide, the vectors, peptides, polypeptides, antibodies and cells of the invention as well as compounds identified in accordance with a method of the invention described hereinabove for the preparation of a pharmaceutical composition for the treatment of diseases involving T-cell activation and associated with Th1 and Th2 immune response, for the treatment of acute and chronic rejection of allo-and xeno organ transplants and bone marrow transplantation, for the treatment of rheumatoid arthritis, lupus erythramatodes, multiple sklerosis, encephalitis, vasculitis, diabetes mellitus, pancreatitis, gastritis, thyroiditis, for the treatment of maligne disorders of T, B or NK cells, for the treatment of asthma, lepramatosis, *Helicobacter pylori* associated gastritis or for the treatment of skin tumors, adrenal tumors or lung tumors.

The polynucleotides, vectors, cells, proteins, (poly)peptides, antibodies, inhibitors, activators, pharmaceutical compositions, uses and methods of the invention can be used for the treatment of all kinds of diseases hitherto unknown as being related to or dependent on the modulation of T-cells. The pharmaceutical compositions, methods and uses of the present invention may be desirably employed in humans, although animal treatment is also encompassed by the methods and uses described herein.

These and other embodiments are disclosed and encompasses by the description and Examples of the present invention. Further literature concerning any one of the antibodies, methods, uses and compounds to be employed in accordance with the present invention may be retrieved from public libraries and databases, using for example electronic devices. For example the public database "Medline" may be utilized which is available on the Internet, for example under www.ncbi.nlm.nih.gov/PubMed/medline.html. Further databases and addresses, such as www.ncbi.nlm.nih.gov/, www.tigr.org/, are known to the person skilled in the art and can also be obtained using, e.g., www.lycos.com. An overview of patent information in biotechnology and a survey of relevant sources of patent information useful for retrospective searching and for current awareness is given in Berks, TIBTECH 12(1994), 352-364.

BRIEF DESCRIPTION OF DRAWINGS

This disclosure may best be understood in conjunction with the accompanying drawings, incorporated herein by references, which show.

A better understanding of the present invention and of its many advantages will be had from the following examples, given by way of illustration.

EXAMPLES

Example 1

Figure 1A:
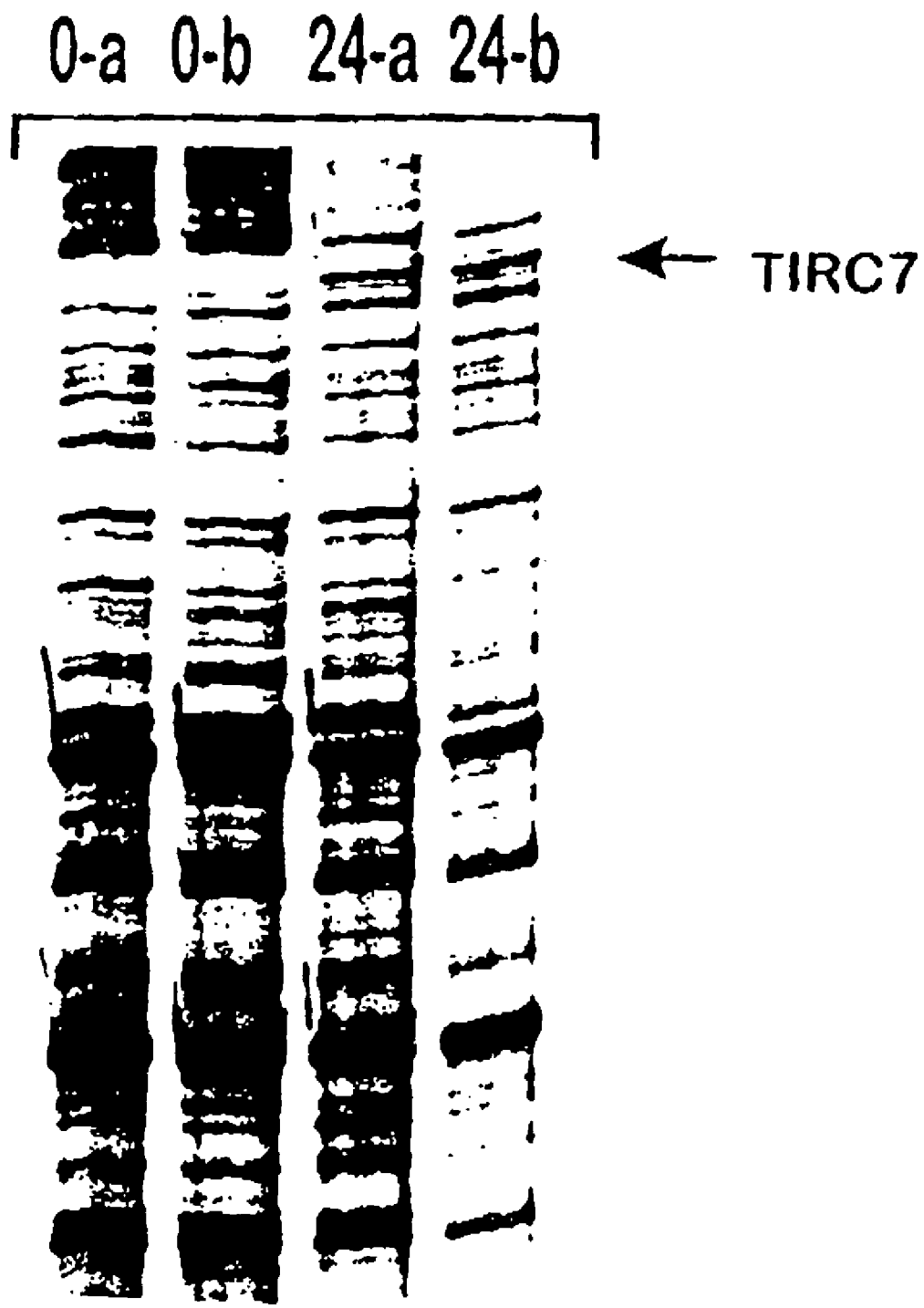
FIG. 1: Identification of TIRC7 from alloactivated T cells.
(A). Differential display identification of a 350 bp transcript upregulated 24 hours after alloactivation of human T lymphocytes. Each lane shows a mRNA expression pattern from a one-way MLR at either 0 or 24 h after activation. Two different MLRs (a and b) exhibited similar patterns of gene expression.
(B). Nucleotide sequence of TIRC7 cDNA. The cDNA and deduced 614 amino acid sequences of the TIRC7 transcript is shown. Predicted transmembrane regions are underlined and bold.
Figure 2:
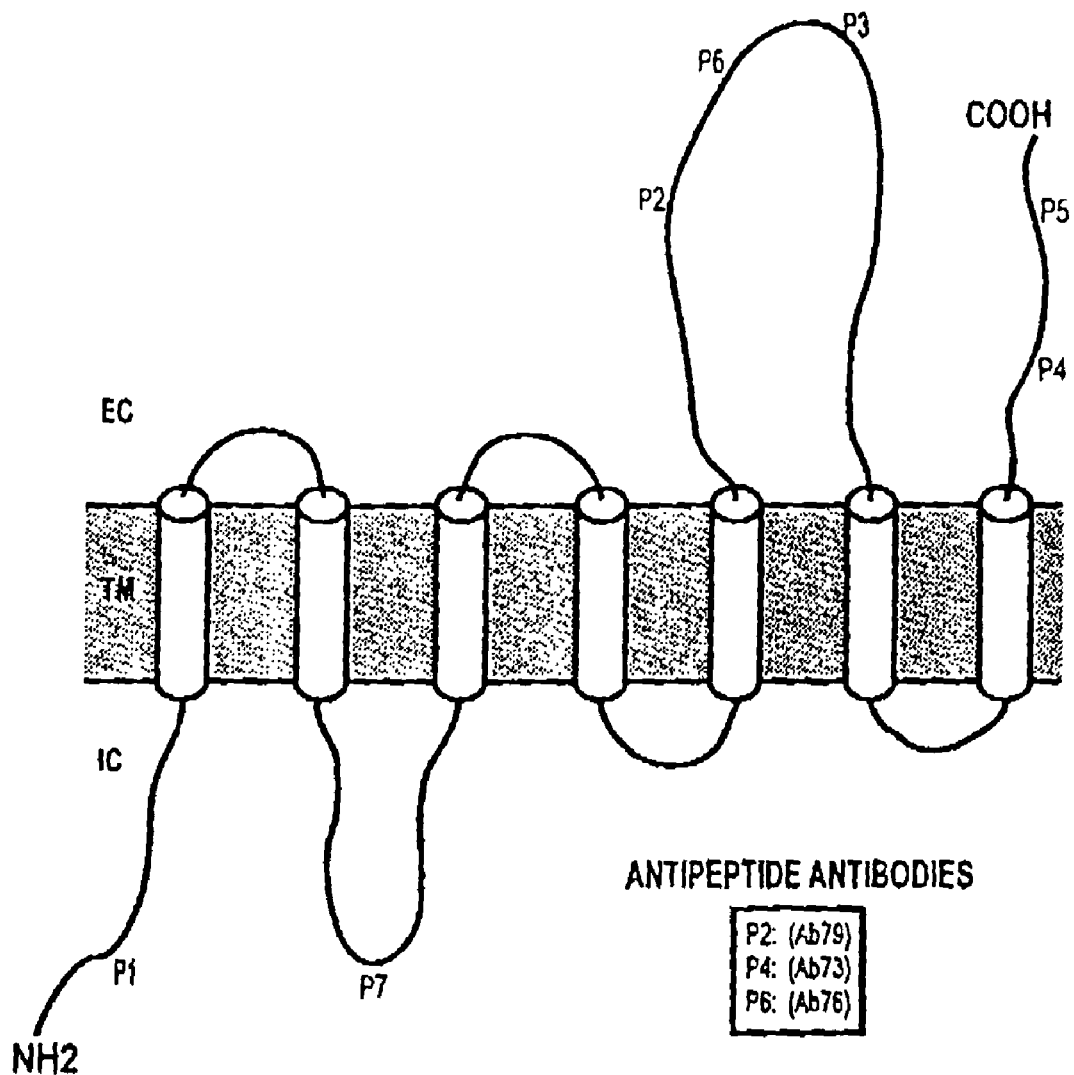
FIG. 2: Predicted secondary structure of TIRC7.
The predicted secondary structure of TIRC7 protein contains seven transmembrane spanning domains (TM). Peptides (P1-P7) synthesized according to sequences in the putative intracellular amino terminus ($NH_3$), extracellular carboxy terminus (COOH), and the largest intracellular (IC) and extracellular (EC) loop were used to raise rabbit anti-TIRC7 polyclonal antibodies. Anti-TIRC7 antibodies with T cell response modulatory effect are given in the box.

Cloning of a Novel Membrane Protein (TIRC7) Encoding a Gene that is Differentially Expressed in Alloactivated Human T Cells To identify novel genes induced during the early stages of T cell activation in response to alloantigens, differential display RT-PCR analysis of mRNA expression was performed at time 0 and 24 h after initiation of a human mixed lymphocyte culture (MLR). In conformance with institutional policies regarding human experimentation, peripheral blood lymphocytes (PBLs) were isolated from healthy human volunteers using standard Ficoll centrifugation methods and diluted into RPMI containing 10% fetal calf serum. Responder PBLs were stimulated with equal numbers of irradiated (3000 rad, 13 min) stimulator PBLs. Cells were co-cultured for 24 h in tissue flasks at an initial concentration of $10^6$ cells/ml for RNA isolation. Total RNA was isolated from MLR at 0 and 24 h using the RNAzol B method (Tel-Test, Inc) and differential display was performed as described previously (Kojima et al., 1996). Briefly, 2 μg of total RNA was reverse transcribed using an oligo-dT primer and 200 U MMLV reverse transcriptase (Gibco/BRL). A 40 cycle PCR amplification with a total volume of 10 μl was performed by using 1 μg of cDNA, 1.25 mM $MgCl_2$, 50 mM KCl, 10 mM Tris-HCl (pH 8.3), 2.5 nM primer, 5 μCi$^{35}$S-dATP, and 0.3 U Taq polymerase. The primers for the PCR amplification were: 5'-GACGGAA-CAGCTTC-3' (SEQ ID No. 10) and 5'-TGCGTCTGGTTCT-3' (SEQ ID No. 11). The PCR products were stored at 4° C. and separated by electrophoresis in 6% polyacrylamide-urea gels, transferred to filter paper, dried, and autoradiographed. The differentially expressed cDNA fragment was excised from the gel, eluted, reamplifed, cloned into pBluescriptSK$^+$ plasmid, and sequenced at the Howard Hughes Biopolymers Research Facility or the Dana Farber Cancer Institute Biopolymer Facility at Harvard Medical School. Homology searches were performed using BLAST at NCBI. Alignments were performed using Geneworks 2.1.1. As shown in FIG. 1A, a 350 bp cDNA fragment was identified which was induced at 24 h after stimulation, and was used to identify several clones from λ-gt-10 cDNA libraries from human T cells. A λ gt-10 cDNA library (Clontech) prepared from human T cells activated for 48 hr with PHA was screened with the 350 bp TIRC7 cDNA fragment. Briefly, plaque lifts of 1,200,000 independent cDNA clones were hybridized with a $^{32}$P-labeled cDNA for 24 hrs at 42° C. in 40% formamide, 10% dextran sulfate, 4×SSC (1×SSC consists of 150 mM NaCl, 15 mM sodium citrate, pH 7.0), 0.8× Denhardt's solution (1× Denhardt's contains of 0.02% polyvinylpyrolidone, 0.02% Ficoll, 0.02% bovine serum albumin), 0.5% sodium dodecyl sulfate (SDS), and 20 mg salmon sperm DNA. The filters were washed twice for 20 min at room temperature with 2×SSC, 10% SDS and for 30 min at 65° C. with 0.2×SSC, 10% SDS followed by autoradiography. Three positive clones were selected and plaque purified. cDNA was sequenced in both directions using a primer walking strategy. A PAC genomic library was screened using a 2 kb cDNA probe containing the ORF cDNA of TIRC7, and the entire genomic cDNA of TIRC7 and OC116 was bidirectionally sequenced. Sequence analysis revealed a 2488 bp cDNA (SEQ ID NO: 1) which was designated as TIRC7 (T cell immune response cDNA7; Gen Bank Accession Number: AF025374), containing an open reading frame of 1842 nt and predicting a protein length of 614 amino acids (SEQ ID No. 2) (FIG. 1B). Furthermore, a second cDNA of TIRC7 was cloned (SEQ ID No. 12) encoding an amino acid sequence that is identical to that of the protein. encoded by the other TIRC7 cDNA except for one amino acid substitution at amino acid position 121 (Arg→Gln). It was therefore concluded that both cDNAs represent alleles of the TIRC7 encoding gene. Hydrophobicity analysis of the protein sequence revealed seven hydrophobic domains, compatible with transmembrane spanning domains. The N-terminus of TIRC7 lacks a consensus signal peptide sequence and followed by seven hydrophobic domains predicting a topology of an intracellular N-terminus and extracellularly oriented C-domain (FIG. 2). TIRC7 contains multiple putative sites of post-translational modification including phosphorylation sites for PKC (at amino acids 58, 98, and 148) and PKA (at amino acid 21), as well as N-linked glycosylation sites (at amino acid 267 and 287). No amino acid homology was found with any proteins known to be involved in T cell activation. TIRC7 does share amino acid homology (12-83%) with several proteins reported as putative subunits of the vacuolar proton pump H$^+$-ATPase (VPP) in a variety of species (Bowman et al., 1988; Lee et al., 1990; Peng et al., 1994; Perin et al., 1991, Manolson et al., 1992, Manolson et al., 1994; Solioz and Davies., 1994; Li et al., 1996). Analysis of the complete genomic DNA organization of TIRC7 revealed that TIRC7 and a recently reported human osteoclast specific cDNA, named OC116 (Li et al., 1996), are alternatively spliced transcripts of the same gene. The function of OC116 is so far unknown and the 2640 nt mRNA, encoding a 814 residue protein, was demonstrated to be exclusively expressed in human osteoclast cells. The regions of strongest homology between TIRC7 and these putative VPPs are predominantly in their predicted transmembrane domains and the C-termini. Thus, TIRC7 belongs to a larger family of structurally related membrane proteins whose functions have not been clearly elucidated.

Figure 3A:
FIG. 3: TIRC7 is upregulated in T cell activation and is localized on the cell membrane.
(A). TIRC7 mRNA expression is upregulated in allostimulated human T cells. MLR-0 and MLR-24 indicate time points 0 h and 24 h, respectively, after coincubation of allogenic responder and stimulator lymphocytes.
(B). TIRC7 mRNA upregulation in MLR (24h) is prevented by Cyclosporin A (Cyc A).
Figure 3B:

To determine the expression kinetics of TIRC7, Northern blot analysis of total RNA from alloantigen activated lymphocytes was performed. Northern blots were prepared with 7-10 μg of total RNA as described previously (Kojima et al., 1996). Poly(A)+ Northern blots containing RNA from various human tissues were purchased from Clontech. Northern blots were probed with the full-length TIRC7 cDNA or a TIRC7-specific cDNA fragment (nt 52-391). Overnight hybridizations were performed with $^{32}$p labeled cDNA probes ($10^6$ cpm/μl) at 42° C. in 40% formamide, 10% dextran sulfate, 4×SSC, 7 mM Tris (pH 7.6), 0.8× Denhardt's solution, 0.02 mg/ml salmon sperm DNA, and 10% SDS. Blots were washed twice in 2×SSC and 0.1% SDS for 20 min at room temperature, once at 65° C. in 0.2×SSC, 0.1% SDS and autoradiographed at −80° C. A TIRC7 specific cDNA probe detected the expected 2.5 kb transcript as well as an additional 4 kb mRNA of unknown origin (FIG. 3A-B). Alloactivation of T cells resulted in a 20-fold upregulation of TIRC7 expression at 24 h (FIG. 3A). TIRC7 expression was transient with no increase at 1 h, peak expression at 24 h, and a return to baseline at 72 h. To demonstrate that the upregulation of TIRC7 occurred in the responder T cell population, an additional MLR was performed using stimulators depleted of T cells. For studies on induction or inhibition of TIRC7 expression, PBLs were exposed to concanavalin A (10 ng/ml), phytohemagglutinin (PHA) (20 mg/ml), *Staphylococcus aureus* enterotoxin B (10 μg/ml), OKT3-mAb (10 mg/ml), cyclosporine A (1 mg/ml) or rIL-2 (10 U/ml). The stimulation with OKT3-mAb was carried out by immobilizing the antibody on plastic culture plates overnight at 4° C. before adding the cell suspension. For RNA isolation from CD4+ and CD8+ human T cells PBLs were incubated with immunomagnetic beads coated with anti-CD4 or anti-CD8 IgG and then subjected to magnetic separation. TIRC7 mRNA expression was found to be increased in responder T cells 24 h after co-culture.

Cyclosporine A (Cyc A), an inhibitor of the calcineurin dependent T cell activation-pathways, blocked the induction of TIRC7 in a MLR (FIG. 3B). Furthermore, exogenous IL-2 was a potent inducer of TIRC7 expression, whereas a modest increase in TIRC7 expression was observed with *Staphylococcus aureus* enterotoxin B (SEB) or OKT3-mAb stimulation after 24 h, though OKT3-mAb increased TIRC7 expression after 48 h to similar levels induced by alloantigen. In contrast, neither concanavalin A (ConA) nor phytohemagglutinin (PHA) increased TIRC7 expression at 24 or 48 h.

Northern analysis revealed that TIRC7 is almost exclusively expressed in immune tissues and exhibits high levels of mRNA expression in spleen, lymph nodes, peripheral blood, and appendix, whereas lower levels of expression are observed in bone marrow, fetal liver and thymus, respectively. TIRC7 was also detected in CD4+ and CD8+ lymphocytes but not in EBV-transformed primary B cells, Burkitt's lymphoma cells, EBV-infected Burkitt's lymphoma cells, and resting or activated Jurkat cells.

Figure 4:
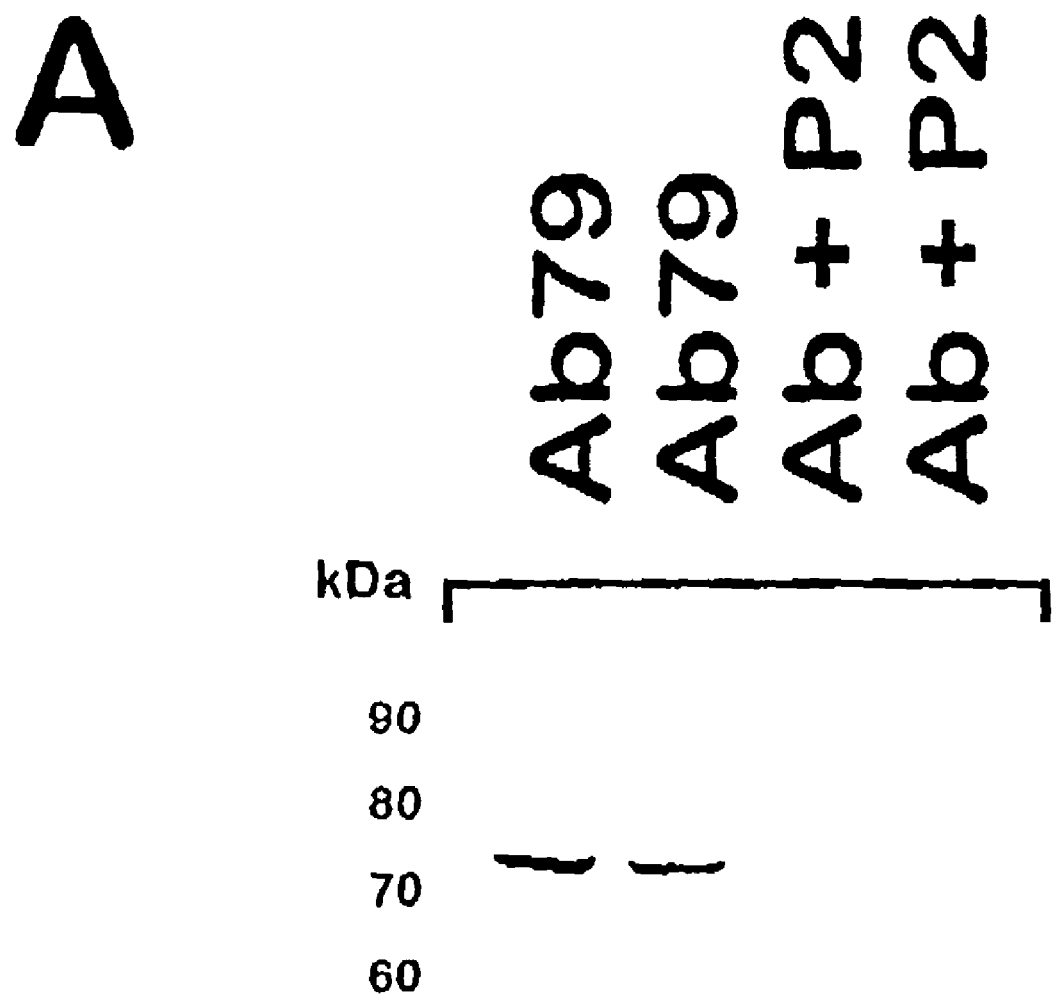
FIG. 4: Localization of TIRC7 protein.
(A). A single 75 kDa protein is detected by anti-TIRC7 antibodies (Ab79 is shown) predominantly in membrane protein extracts of human lymphocytes. Binding of Ab79 to TIRC7 is abolished in the presence of the respective peptide P2 (Ab+P2).
(B). The same single 75 kDa protein is also detected by an anti-c-myc antibody in membrane preparations of COS-7 cells transiently transfected with a c-myc tagged TIRC7 expression vector (COS7-t) but not in untransfected COS-7 cells (COS7-nt).
Figure 4:
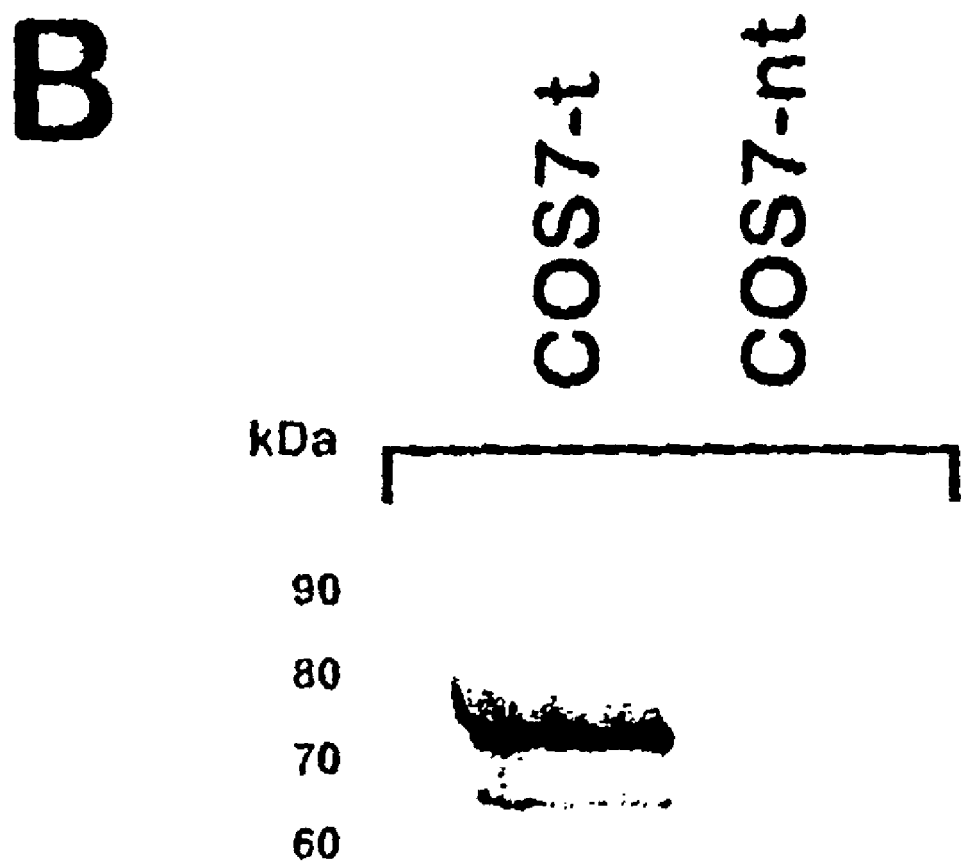

In Western blot analysis, a single protein of approximately 75 kDa molecular mass was detected predominantly in membrane extracts of human lymphocytes (FIG. 4A). PBLs were lysed in 50 mM Tris (pH 7.59), 150 mM NaCl, 1% triton, aprotinin (0.15 U/ml), 20 mM leupeptin, and 1 mM phenlymethylsulfonylfluoride. Lysates were separated by SDS-PAGE and transferred to a nitrocellulose membrane. The membranes were incubated with primary (see Example 2, infra) and secondary antibody for 1 h each, and bound primary antibody was detected by horseradish peroxidase-conjugated secondary antibody followed by enhanced chemi-lumi-nescence (Boehringer). Polyclonal Ab79 (see Example 2, infra) was used at 1:5000 dilution. The secondary antibody (anti-rabbit-IgG) conjugated with peroxidase was used at 1:2000 dilution. To detect the TIRC7/c-myc fusion protein the anti-c-myc antibody was used at 1:1000 dilution and the secondary antibody (anti-mouse-IgG) used at 1:2000 dilution. The same protein was found in membrane preparations from CHO cells and COS-7 cells (FIG. 4B) stably and transiently transfected with a c-myc tagged TIRC7 expression vector, respectively. The full-length TIRC7 ORF was cloned upstream of a c-myc epitope sequence to create a fusion protein construct in a mammalian expression vector (Progmega). Transient transfection of COS7 cells and stable transfection of CHO cells was performed by lipofectamine transfection method as described (Schülein et al., 1996). An anti-c-myc antibody (InVitrogen) was used to detect the protein. TIRC7 localization to the cell membrane was confirmed by confocal microscopy and flow cytometric analysis in human lymphocytes as well as in stably transfected CHO cells.

Example 2

TIRC7 Mediates an Essential Signal during Early Events of T Cell Activation

Figure 5A:
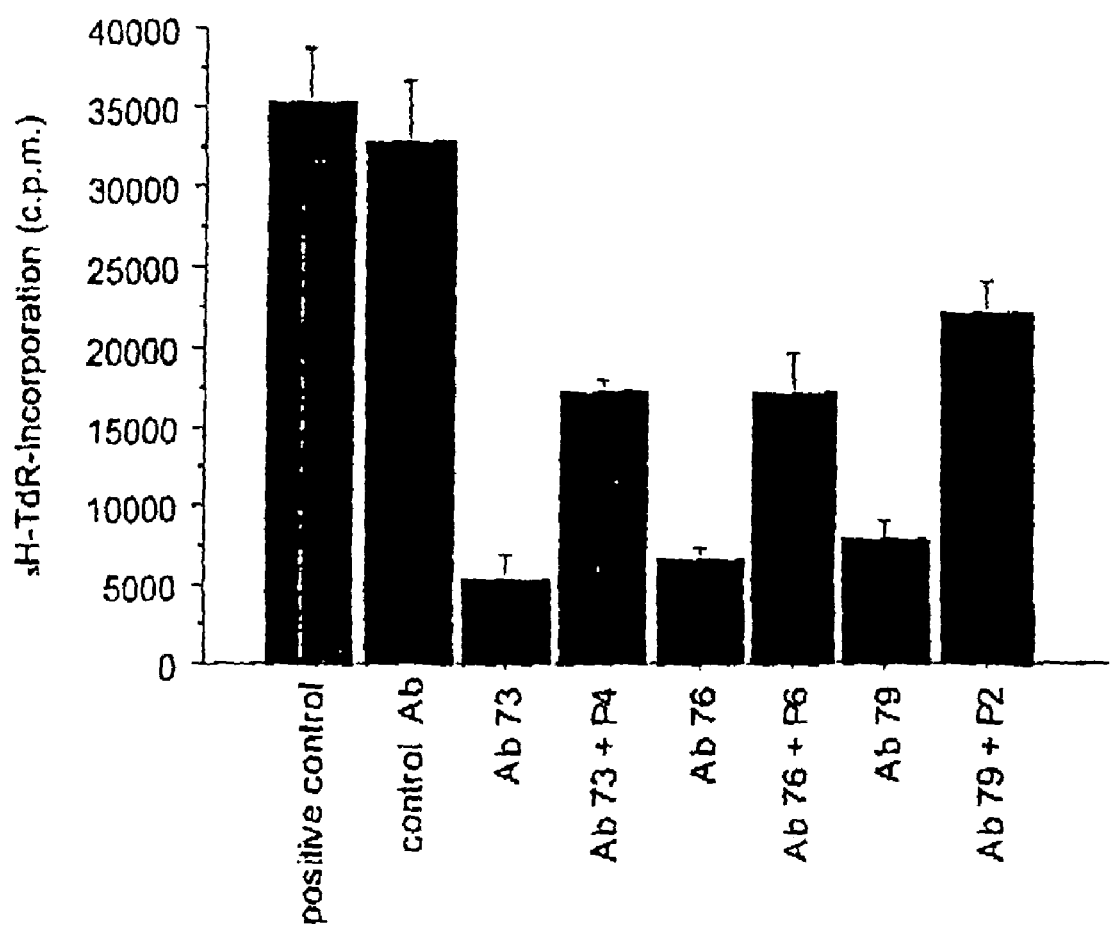
FIG. 5: Anti-TIRC7 antibodies inhibit T cell proliferation and IL-2 production.
(A). Anti-TIRC7 antibodies (Ab73, Ab76, Ab79) directed against extracellularly located TIRC7 peptides (P4, P6, P2) inhibit proliferation in alloantigen stimulated T cells as determined by [$^3$H]-thymidine incorporation. Inhibition was diminished when antibodies were preincubated with their respective peptides. Proliferation in a MLR after 24 h is displayed as positive control. Proliferation was not affected by preimmune serum (control Ab). Each bar represents mean and SD from seven independent experiments.
(B). Inhibition of proliferation by exogenous TIRC7 protein. In a one-way MLR in vitro translated TIRC7 protein inhibited proliferation in a dose-dependent manner. Protein dilutions are indicated. No inhibition of proliferation was observed when vector alone (vector) or an unrelated cDNA (unrel) was used in the in vitro translation preparation.
(C). Anti-TIRC7 antibodies inhibit Th1 specific cytokine expression. PHA stimulated human lymphocytes were coincubated with Ab73, Ab76 and Ab79, respectively. Supernatants of mitogen stimulated cultures were taken at 24 and 48 h. Cytokine expression in the supernatants were determined by ELISA. Each bar represents mean and SD from three independent experiments.
(D). Anti-TIRC7 antibody mediated inhibition of proliferation of PHA activated T cells is reconstituted by exogeneous IL-2. Each bar represents mean and SD from three independent experiments.

The functional significance of a number of proteins required in T cell activation has been determined by modulation of their signaling by targeting with specific antibodies. To examiner whether antibodies directed against TIRC7 could alter the T cell proliferative response, seven synthetic peptides representing different domains of the TIRC7 protein (P1-P7, SEQ ID NOs. 8, 3, 4, 5, 6, 7 and 9, respectively) were used to produce polyclonal rabbit antipeptide antibodies (FIG. 2). Antigenic non-transmembrane regions of TIRC7 were identified using PSORT and PC-GENE and used to design short peptide sequences. Purified synthetic peptides (P1-P7) (Laboratories of Heinklein, Berlin, Germany) were used for immunization of rabbits (Seramun, Berlin, Germany). Animals were boostered after three and six weeks. A total of 14 polyclonal antibodies were prepared against 7 different peptides (P1-P7). The pooled antisera were purified by affinity chromatography after binding of peptide to BSA. All antibodies were tested by ELISA with their respective peptides. As shown in FIG. 5A, three of the antibodies Ab73, Ab76 and Ab79, which were directed against the extracellularly located domains P4, P6 and P2 (SEQ ID Nos. 5, 7 and 3), respectively, were found to inhibit the proliferation of alloactivated T cells by 87-93%. For proliferation assays, responder PBLs were plated in the presence of an equal number of irradiated-stimulator cells (total of 2×$10^6$ cells /ml) with either media alone, antibodies or control serum into each well of a round-bottomed 96-well microtiter plate in a final culture volume of 200 μl. Anti-TIRC7 anti-sera were added in 1:500 dilutions to MLR. The plates were incubated at 37° C., 5% $CO_2$ and pulsed for the final 18 h of the culture with 1 μCi [$^3$H]-thymidine (ICN Biochemicals) per well. All plates were harvested and counted on a Betaplate liquid scintillation counter. Counts were represented as the mean cpm of quadruplicate wells harvested at 72 h following the 18 hr pulse. To prevent complement lysis of the cells, antibodies were incubated at 52° C. for 20 min prior to use. Peptide blocking experiments were performed by coincubation of the antibody with the appropriate peptide for 30 min at 4° C. prior to initiating the $MLR_G$. For studies using TIRC7 protein, serial dilutions (1:200, 1:300, 1:600) of the dialyzed in vitro translated TIRC7 protein were added to MLRs and inhibition was measured by $^3$H-thymidine incorporation. The cytokine expression for IL-2, IL-4 and interferon-γ were detected in culture supernatants by ELISA. Commercial kits were used for IL-2 (Laboserv), IL-4 (Laboserv) and IFN-γ (Medgenix). The anti-TIRC7 antibodies inhibited T cell proliferation in a dose dependent manner. Inhibition was diminished when the respective peptides were added to the reaction to specifically neutralize the antibody. The antibodies had no effect when added 24 h -72 h after initiating the MLR, indicating that the TIRC7 mediated signal was specific for an early event in the T cell response. These three anti-TIRC7 antibodies also caused efficient inhibition of T-cell activation induced by ConA, PHA, and OKT3-mAb, respectively.

Figure 5B:
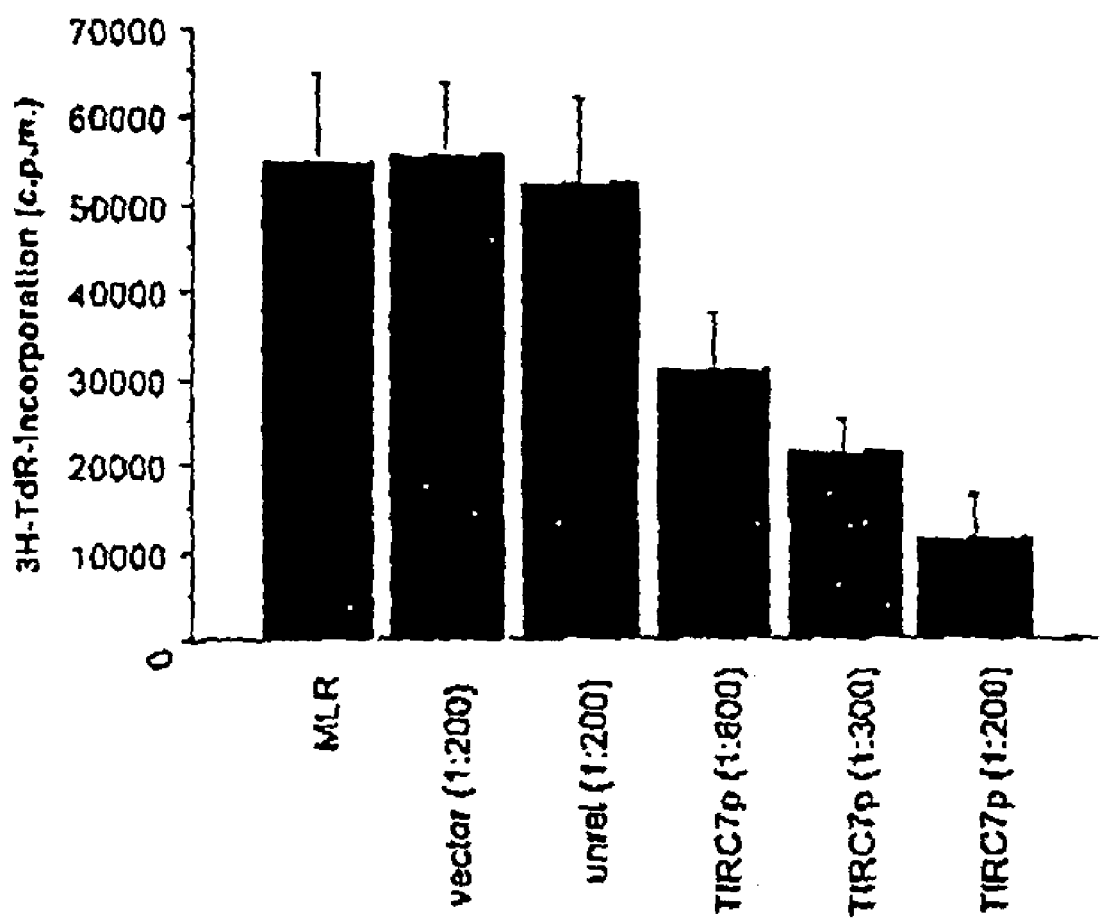

Membrane proteins associated with T cell activation are often involved in ligand-receptor interactions that can be blocked by exogenous soluble protein, as has been demonstrated by blocking of CD28/B7 interaction with the soluble protein CTLA4Ig (Linsley et al., 1992). In vitro translated TIRC7 protein was therefore tested for its ability to inhibit the MLR by adding it to MLR cultures at time 0 at dilutions of 1:200, 1:300,1:600. 2 µg of TIRC7 cDNA were translated in an in vitro translation TNT lysate system (Promega) containing $^{35}$S methionine (ICN). The product was visualized by SDS-page (11%) and autoradiography. For MLR inhibition experiments, TIRC7 protein was synthesized in vitro in the presence of microsomal membranes. The in vitro translation mixture was then suspended in 500 µl PBS and dialyzed against PBS for 24 h. As shown in FIG. 5B, exogenous TIRC7 protein significantly suppressed the proliferation of alloreactive T cells in a dose-dependent manner. In control experiments, no inhibition was seen using either vector alone (FIG. 5B) or another unrelated cDNA in the in vitro translation reaction mixture.

Example 3

Targeting of the TIRC7 Mediated Signal Inhibits Th1 Specific Cytokine Expression, which is Reversed by Exogenous rIL-2

Figure 5C:
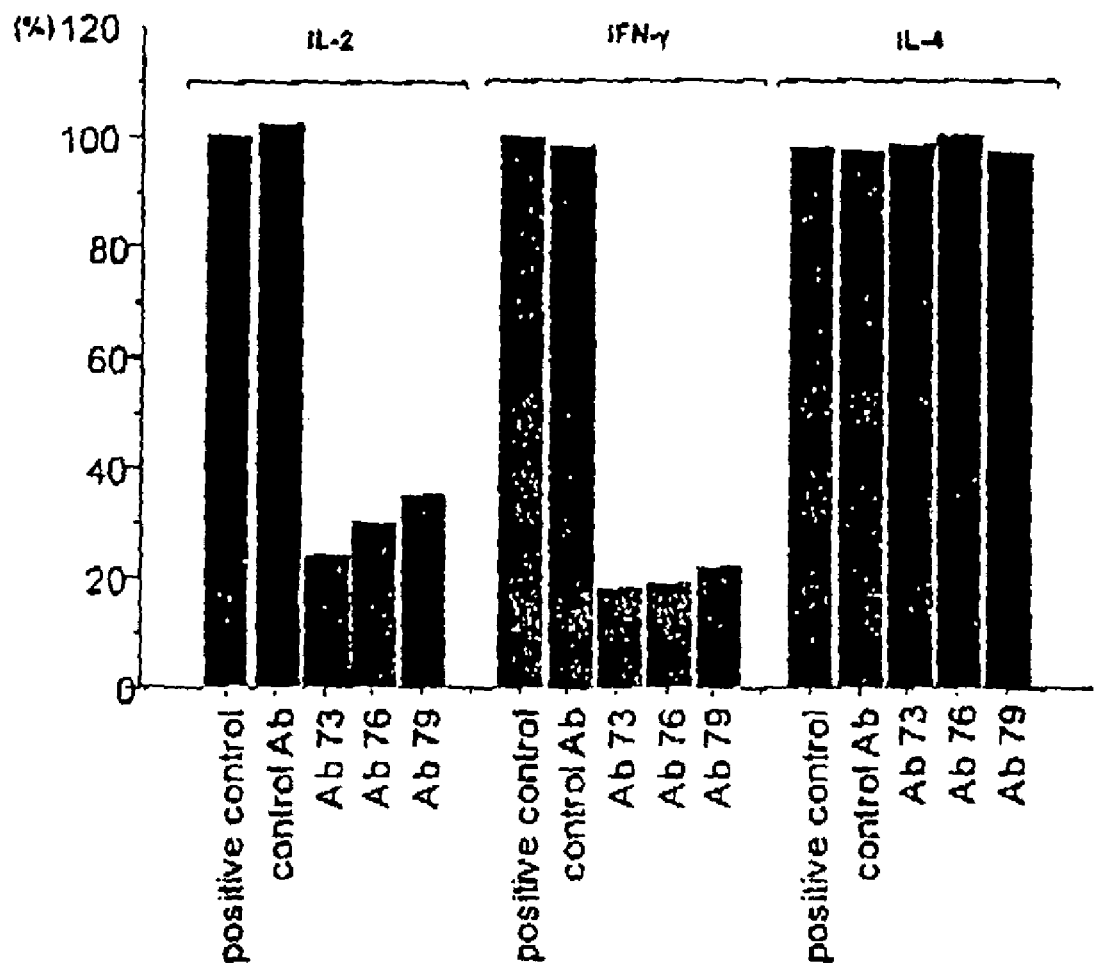
Figure 5D:
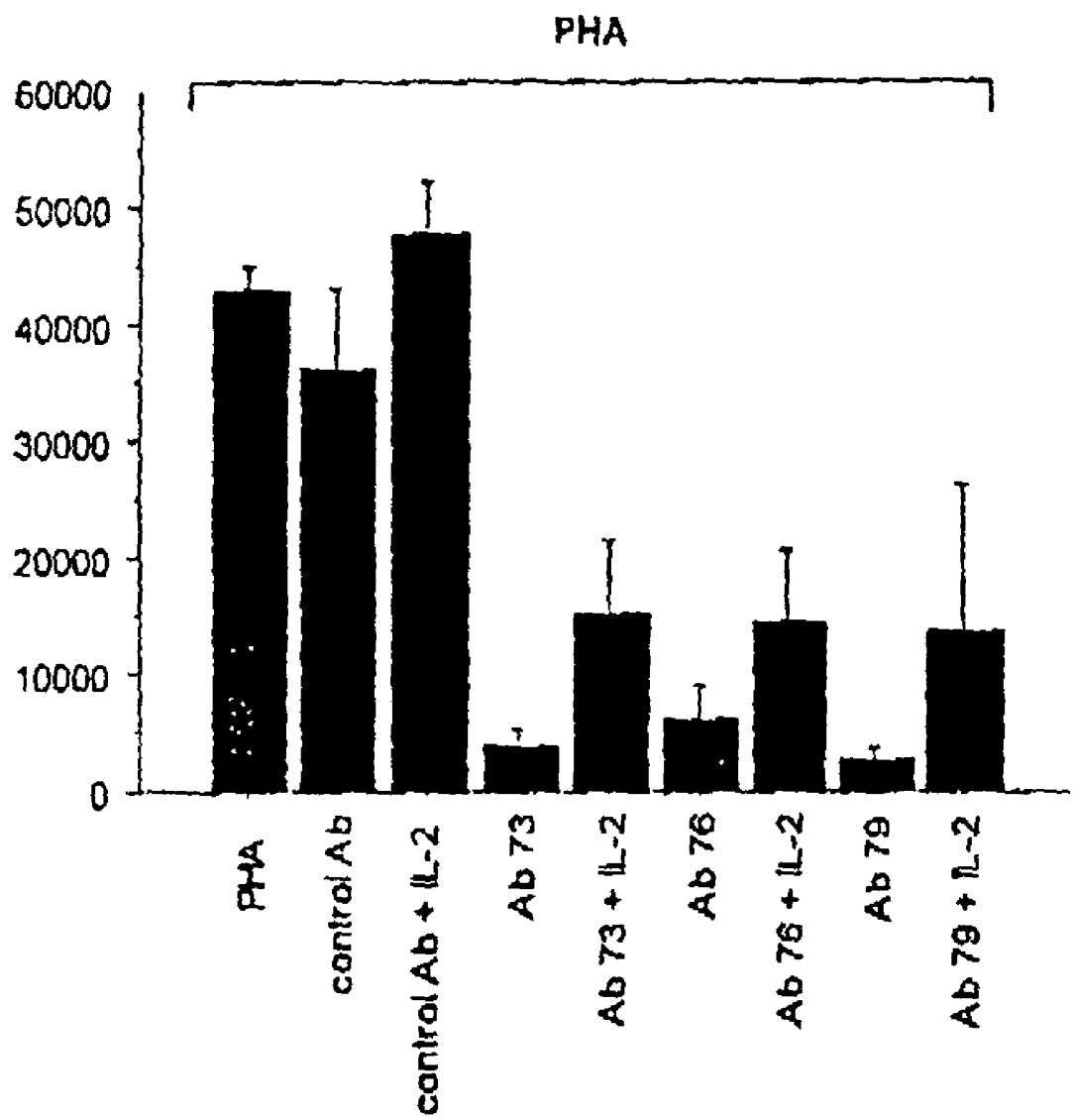

To further differentiate whether signals mediated by TIRC7 differentially affect T cell subsets, human T cells were challenged with either OKT3-mAb, ConA or PHA, and the cytokine profiles specific for Th1 and Th2 lymphocyte subsets were analyzed in the presence and absence of anti-TIRC7 antibodies. As shown in FIG. 5C, a significant decrease of the Th1-specific cytokines IL-2 and IFN-γ was observed at 48 h in all cultures of PHA stimulated lymphocytes. Of the three mitogens tested, the IL-2 and IFN-γ downregulation occurred in ConA and PHA activated cultures at 24 h, whereas the OKT3-mAb stimulated T cells showed a significant decrease of IL-2 at 24 h but of IFN-γ only after 48 h. No downregulation of IL-4 production, which is specific for Th2 lymphocytes, was observed in any of the mitogen activated T cells after 24 and 48 h. Remarkably, exogenous addition of recombinant IL-2 to mitogen-activated cultures incubated with anti-TIRC7 antibodies reconstituted the diminished T cell proliferation (FIG. 5D).

Example 4

Figure 6:
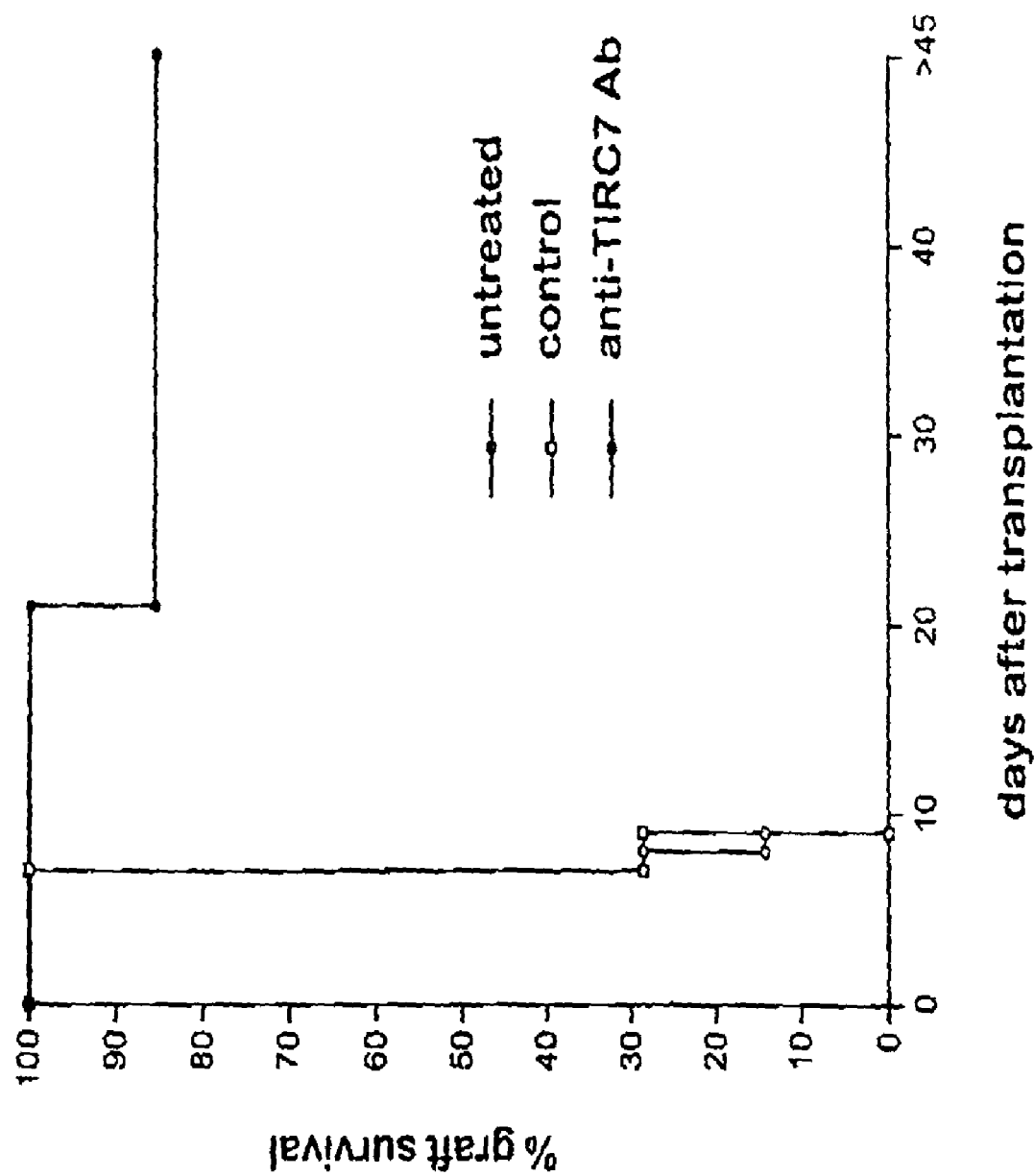
FIG. 6: Anti-TIRC7 antibody targeting in vivo significantly prolongs allograft survival.
- (A). Lewis rat recipients of Wistar Furth rat kidney allografts received either anti-TIRC7 Ab73 (n=7), control antibody from preimmune serum (n=7), or no treatment (n=7). Treatment was initiated at 2 h prior to and immediately after transplantation, and was repeated on day 1, 2, 4, and 6 post-transplantation. Animals treated with control antibody showed a mean survival time of 8±1 days whereas mean survival time of animals representing the untreated control group was 7±2 days. Six of the seven animals in the experimental group maintained functional grafts for more than 45 days. One rat in the anti-TIRC7 antibody treated experimental group had a survival time of 21 days. As assessed at day 45 after transplantation, the mean survival time in this group was 41,5 days (p<0.001 vs controls).
Figure 7A:
FIG. 7: Histological analysis of kidney allografts at day 7 post-transplantation.
- (A). Kidney allografts of rats receiving control antibodies showed severe tissue destruction and diffuse mononuclear infiltration which was similar to histological findings in the kidney allografts of untreated animals.
- (B). Renal allografts of two additional anti-TIRC7 antibody treated animals sacrificed at day 7 showed very mild interstitial infiltration of mononuclear cells. Tissue lessions were not identified in the allografts of these animals.
Figure 7B:

TIRC7 Antibody Targeting Significantly Prolongs Renal Allograft Survival In Vivo The effect of modulating the TIRC7 mediated signal was studied in an animal model featuring kidney transplantation from Wistar Furth to Lewis rats. Male inbred rats 200-250 g (Harlan Winkelmann, Germany) were used throughout the experiment. Wistar Furth rats (WF, RT1$^0$) were grafted into bilaterally nephrectomized Lewis rats (LEW, RT1$^1$) using microsurgical techniques; ischemic time was 30±5 min. Cryostat sections were fixed in formalin. The fixed tissue. was paraffin embedded, and tissue sections were stained with hematoxylin and eosin. In initial experiments, anti-human TIRC7 antibodies were tested for their ability to inhibit the proliferation of Lewis rat lymphocytes stimulated with irradiated Wistar Furth rat lymphocytes in vitro. Ab73 was shown to profoundly block rat T cell proliferation. In kidney transplant experiments, animals remained either untreated (n=7), received preimmune rabbit serum (n=7) or were treated with anti-TIRC7 antibody Ab73 (n=7), 2 h before, directly after and on days 1, 2, 4 and 6 after transplantation. No side effects except for transient mild diarrhea were observed in the anti-TIRC7 antibody treated group. Anti-TIRC7 antibody significantly prolonged the graft survival time of treated animals (p<0, 001). Six of seven allografts of the anti-TIRC7 treated animals remained functional for more than 45 days after completion of antibody administration. One animal treated with anti-TIRC7 antibody died at day 21. In contrast, all animals in both control groups died of renal failure by day 7 to 9 after transplantation (FIG. 6). Histological examination of kidney grafts from two additional antibody treated animals sacrificed at day 7 post-transplantation demonstrated very mild lymphocytic infiltration but no signs of tissue necrosis (FIG. 7B). In contrast, kidney grafts from control animals displayed remarkable evidence of acute graft rejection including diffuse mononuclear cell infiltrates as well as extensive areas of necrosis (FIG. 7A).

Summary: TIRC7 is a novel T-cell accessory protein

TIRC7 represents a novel protein that plays an essential role freesin T cell activation. Early after stimulation of the T cell receptor the level of TIRC7 mRNA is transiently increased. This increase in expression appears to rely on an IL-2 dependent pathway, as upregulation of TIRC7 mRNA is also observed after incubation of T cells with IL-2 and blockade of TIRC7 upregulation is achieved with cyclosporine A. T cell stimulation by mitogens such as ConA or PHA consistently fail to upregulate TIRC7 expression. The pattern of tissue expression suggests that TIRC7 is a product of mature lymphoid cells, as TIRC7 is expressed in all lymphoid tissues with low expression only in thymus, bone marrow and fetal liver. The TIRC7 protein is predominantly expressed on the cell membrane, consistent with a target for an external ligand. The seven transmembrane domain structure predicts three extracellular loops and an extracellularly oriented carboxy terminus.

Anti-TIRC7 antibodies directed against the extracellular domains, but not those recognizing predicted intracellular domains of the protein, are able to efficiently suppress the proliferation of T cells in response to alloactivation in a mixed lymphocyte culture or in response to mitogens. The inhibitory effect of anti-TIRC7 antibodies on T cells induced by a variety of different stimulatory pathways suggests that TIRC7 plays a central role in T cell activation. Moreover, inhibition of T cell proliferation in MLR by antibody targeting of TIRC7 suggest the existence of a ligand specifically interacting with TIRC7. Support for this hypothesis is provided by the dose-dependent inhibition of T cell proliferation in a MLR in the presence of soluble in vitro translated TIRC7 protein.

TIRC7 shares 38% amino acid homology with J6B7, a protein isolated from a mouse T cell line (Lee et al., 1990). Like TIRC7, J6B7 exhibits considerable homology with the putative rat H$^+$-ATPase subunit VPP116 (Manolson et al., 1992). In vitro translated J6B7 protein was demonstrated to inhibit mouse T cell proliferation in a MLR by 89%, which is comparable with the results obtained with in vitro translated soluble TIRC7 protein in human MLR in the present study.

Antibody targeting of TIRC7 has a selective inhibitory effect on the Th1 lymphocyte subset, as evidenced by the inhibition of IL-2 and IFN-γ, but not IL-4, cytokine production. With anti-TIRC7 antibody treatment the cells appear to remain in an unresponsive, but functional, state since exogenous recombinant IL-2 reversed the antiproliferative effect of the anti-TIRC7 antibodies. The ability of an anti-TIRC7 antibody to prevent allograft rejection in the in vivo model of rat kidney transplantation reflects the findings obtained in the in vitro studies. Moreover, the effects of antibody targeting of TIRC7 are quite similar to those observed by targeting of costimulatory molecules. TIRC7 does not share structural or sequence homology with any of the known T cell accessory molecules. Thus, TIRC7 may participitate in a distinct signaling pathway induced early in the course of T cell activation.

Given the functional similarities between TIRC7 and the known T cell accessory molecules, it is expected that the structural novelty of TIRC7 will contribute to the understanding of distinct mechanisms in the T cell response. Moreover, the striking capacity of anti-TIRC7 antibody to significantly prolong allograft survival in vivo provide a novel approach for a selective inhibition of undesired T cell activation in human organ transplantation and autoimmune diseases.

Those skilled in the art will recognize, or be able to ascertain using no more than routine experimentation, many equivalents to the specific embodiments of the invention described herein. Such equivalents are intended to be encompassed by the following claims.

REFERENCES

Abbas, Nature 383 (1996), 787-793
Bachmann, Immunity 7 (1997), 549-557
Blazar J. Immunol. 157 (1996), 3250-3259
Bluestone, Immunity 2 (1995), 555-559
Bowman, J. Biol. Chem. 263 (1988), 13994-14001
Cosimi, Transplantation 32 (1981), 535-539
Crabtree, Science 243 (1989), 355-361
Kirk, Proc. Natl. Acad. Sci. USA 94 (1997), 8789-8794
Kojima, J. Biol. Chem. 271 (1996), 12327-12332
Larsen, Nature 381 (1996), 434-438
Lazarovits, Nature 380 (1996), 717-720
Lee, Mol. Immunol. 27 (1990),.1137-1144
Lenschow, Annu. Rev. Immunol. 14 (1996), 233-58
Lenschow, Science 257 (1992), 789-792
Linsley, Annu. Rev. Immunol. 11 (1993), 191-212
Linsley, Science 257 (1992), 792-95
Li, Biochem. Biophy. Res. Commun. 218 (1996), 813-821
Manolson, J. Exp. Biol. 172 (1992), 105-112
Manolson, . Biol. Chem. 269 (1994) J, 14064-14074
Mohammed, J. Exp. Med. 181 (1995), 1869-1874
Peng, J. Biol. Chem. 269 (1994), 17262-17266
Perez, Immunity 6 (1997), 411-417
Perin, J. Biol. Chem. 266 (1991), 3877-3881
Schreiber, Immunology Today 13 (1992), 136-42
Schülein, J. Biol. Chem. 271 (1996), 28844-28852
Schwartz, Cell 71 (1992), 1065-1068
Solioz, J. Biol. Chem. 269 (1994), 9453-9459
Turka, Proc. Natl. Acad. Sci. USA 89 (1992), 11102-11105
Walunas, Immunity 1 (1994),405-413
Xu, Immunity 1 (1994), 423-431

What is claimed is:

1. An isolated T-cell immune response cDNA7 (TIRC7) membrane protein of approximately 75 kDa capable of inhibiting the proliferation of T-cells in response to alloactivation in a mixed lymphocyte culture or in response to mitogens, the amino acid sequence of which is encoded by a DNA selected from the group consisting of:
   (i) DNA comprising a nucleotide sequence encoding a protein having the amino acid sequence depicted in SEQ ID NO: 2 or SEQ ID NO: 13 from amino acid position 1 to 601; and
   (ii) DNA comprising the nucleotide sequence depicted in SEQ ID NO: 1 or SEQ ID NO: 12.

2. The protein of claim 1, which is in a soluble form.

3. An isolated polypeptide which consists of the amino acid sequence set forth in any of SEQ ID NOS.: 3 to 7.

4. A pharmaceutical composition comprising the protein of claim 1 and a carrier.

5. A method for treating a cell or organ transplant rejection comprising administering to a subject the pharmaceutical composition of claim 4.

6. A method for treating autoimmune disease comprising administering to a subject the pharmaceutical composition of claim 4.

* * * * *